(12) United States Patent
Woehr et al.

(10) Patent No.: US 6,616,630 B1
(45) Date of Patent: *Sep. 9, 2003

(54) SPRING CLIP SAFETY IV CATHETER

(75) Inventors: Kevin Woehr, Felsberg (DE); Manfred Orth, Kassel (DE); Mark Wynkoop, Coopersberg, PA (US)

(73) Assignee: B. Braun Melsungen A.G., Melsungen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/638,641

(22) Filed: Aug. 14, 2000

Related U.S. Application Data

(63) Continuation-in-part of application No. 09/183,697, filed on Oct. 30, 1998, now Pat. No. 6,287,278, which is a continuation-in-part of application No. 09/097,170, filed on Jun. 12, 1998, now Pat. No. 6,117,108, which is a continuation-in-part of application No. 08/915,148, filed on Aug. 20, 1997, now abandoned.

(51) Int. Cl.$^7$ ................................................ A61M 5/00
(52) U.S. Cl. ........................................ 604/110; 604/263
(58) Field of Search ............................ 604/263, 164.01, 604/164.03, 164.04, 164.07, 164.08, 110

(56) References Cited

U.S. PATENT DOCUMENTS 5,135,504 A * 8/1992 McLees ................. 604/164.08

* cited by examiner

Primary Examiner—Brian L. Casler
Assistant Examiner—Kevin C. Sirmons
(74) Attorney, Agent, or Firm—Christie, Parker & Hale, LLP

(57) ABSTRACT

A safety IV catheter includes a unitary, resilient needle guard received in a catheter hub. The needle guard includes a proximal arm or wall that includes an opening through which a needle passes for axial movement. When the needle is retracted from the catheter, it releases the force that had previously prevented movement of the needle guard within the catheter hub. This in turn causes the needle guard to snap into a position in which it is clamped onto the needle shaft and in which its distal wall blocks access to the needle tip. In this condition, the spring needle guard and needle can be removed from the catheter hub. A slot or crimp may be formed in the needle shaft that engages with the needle guard after the protected needle and needle guard are removed from the catheter hub.

53 Claims, 17 Drawing Sheets

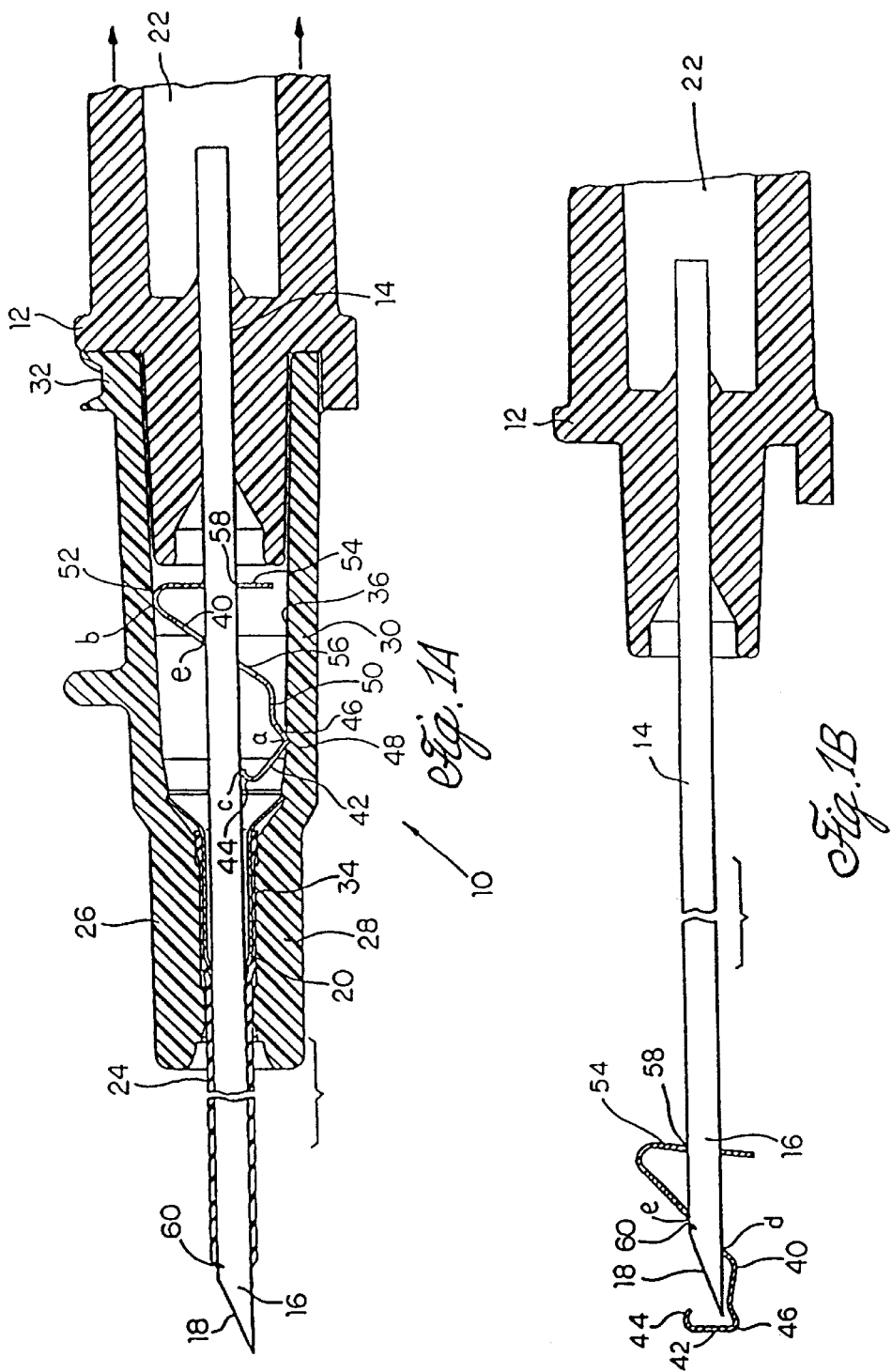

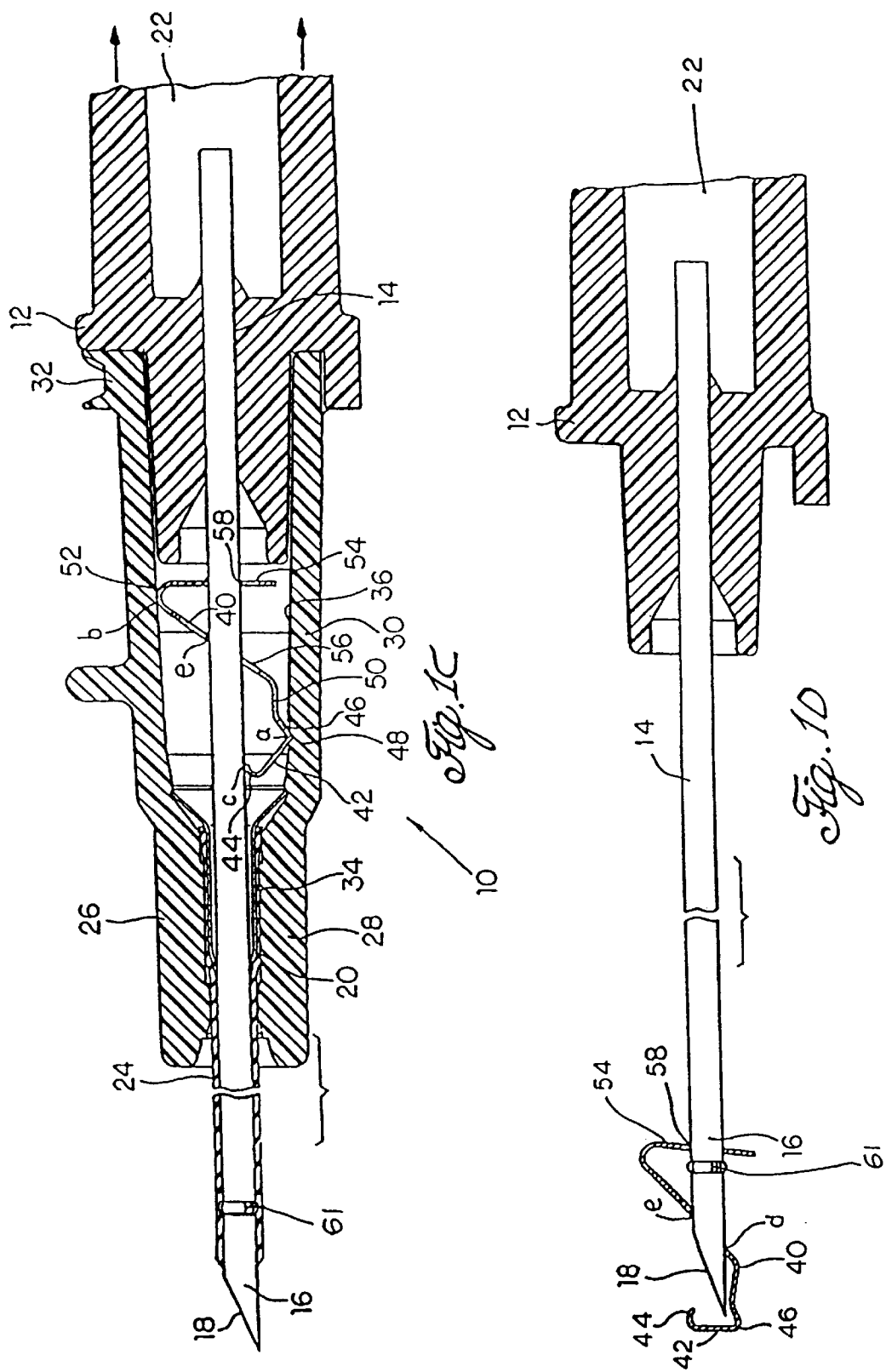

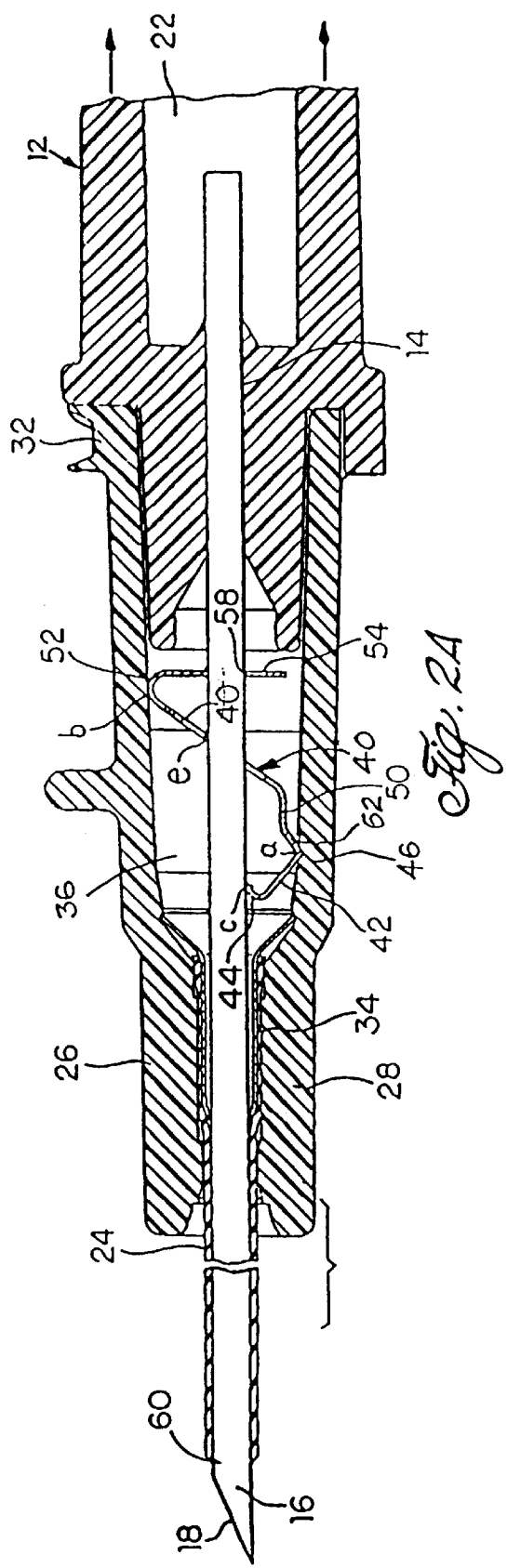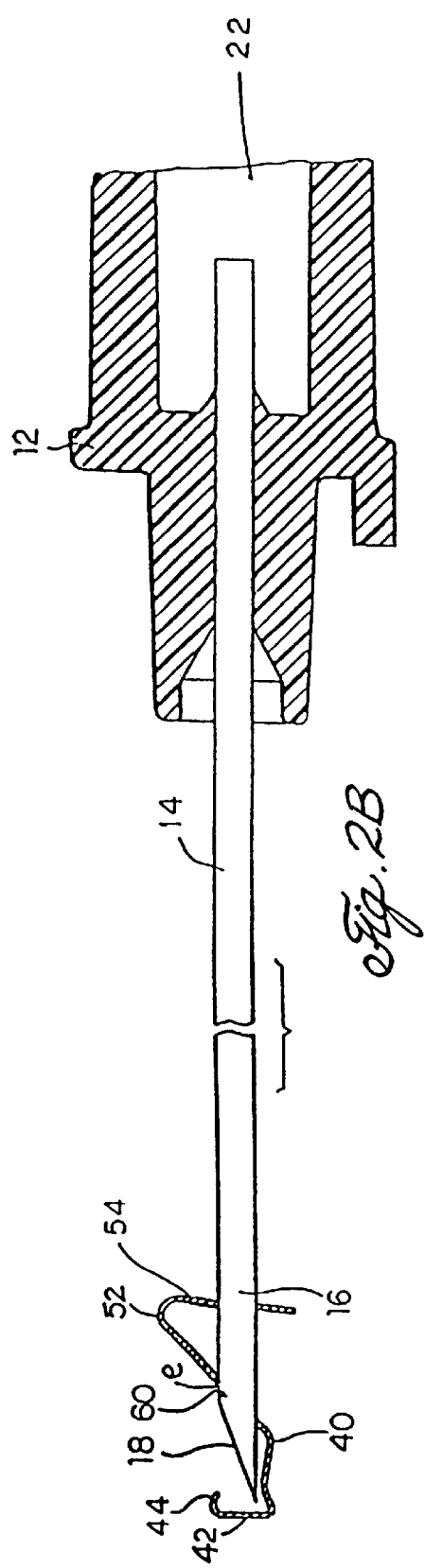

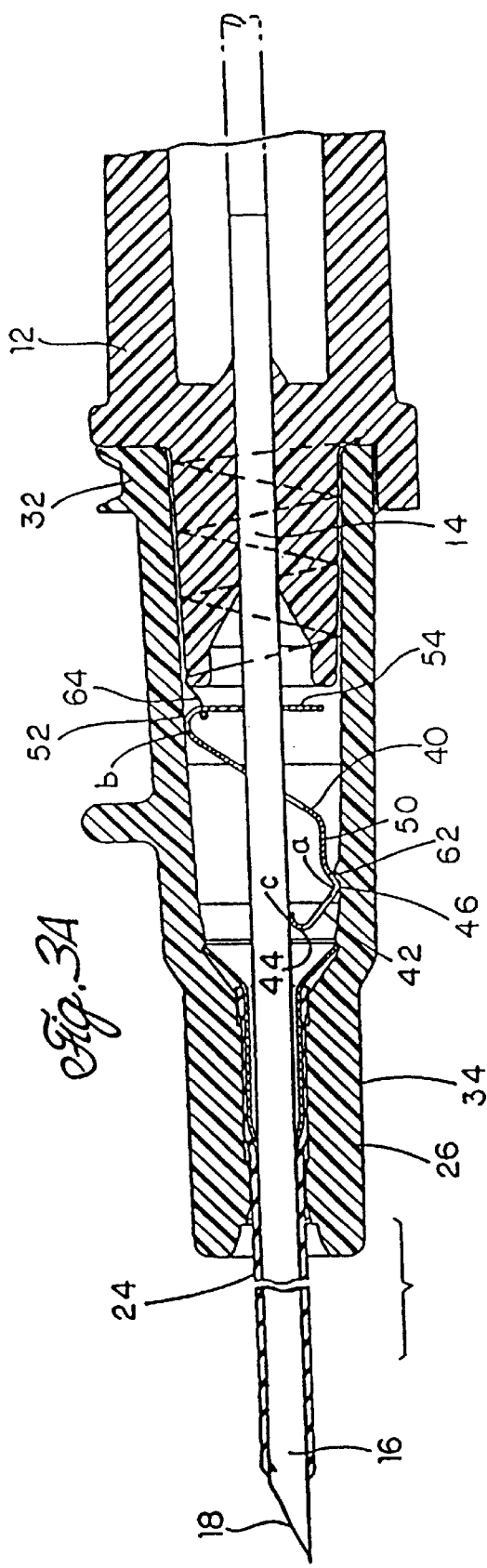
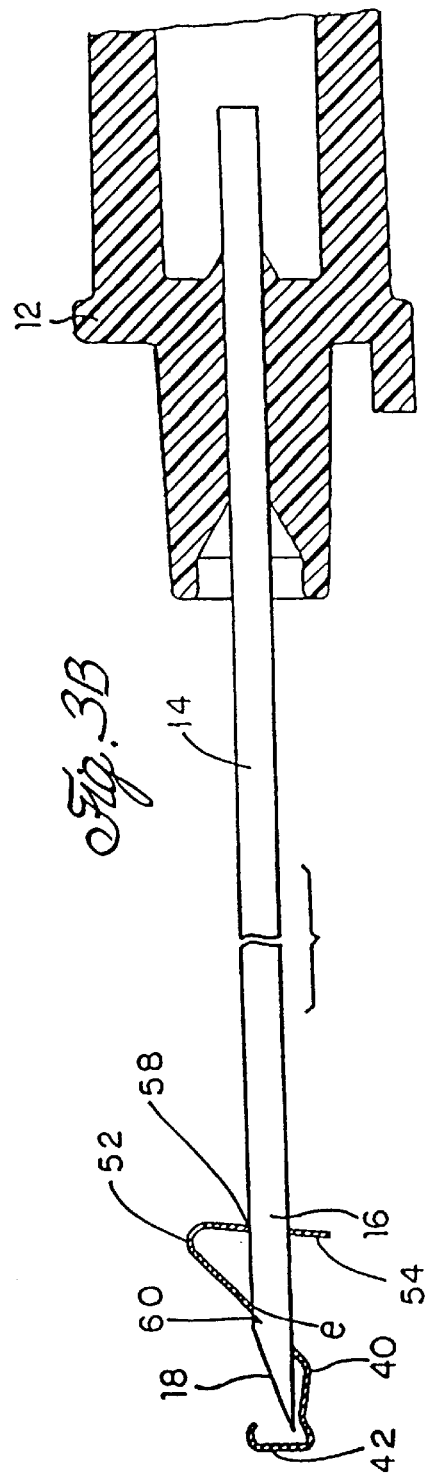

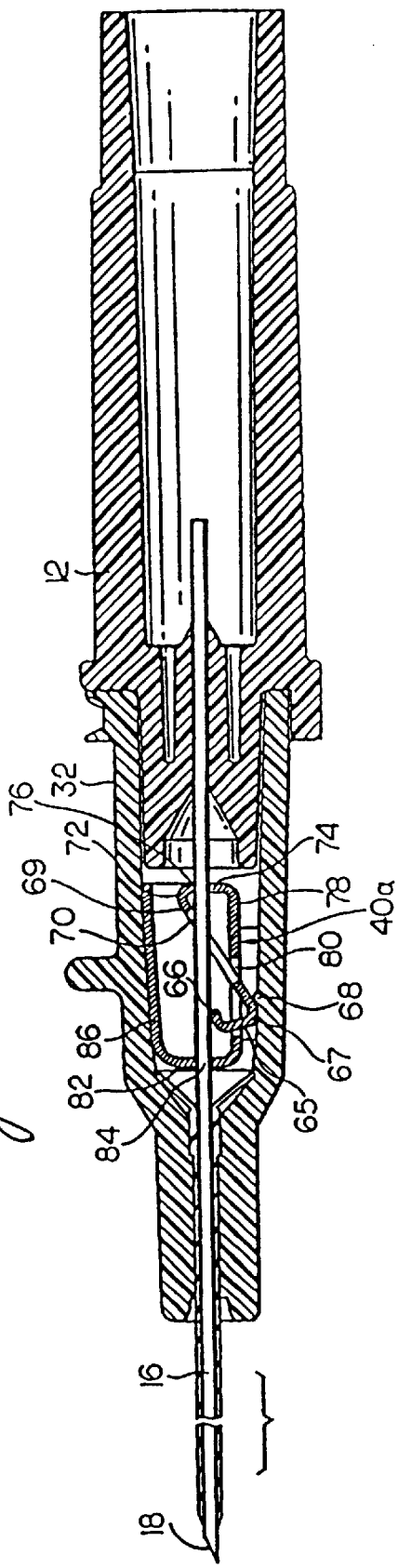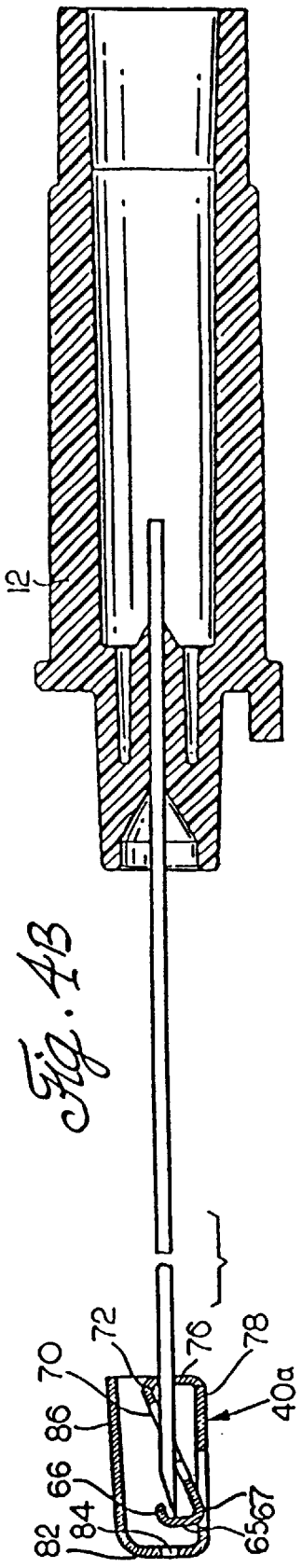

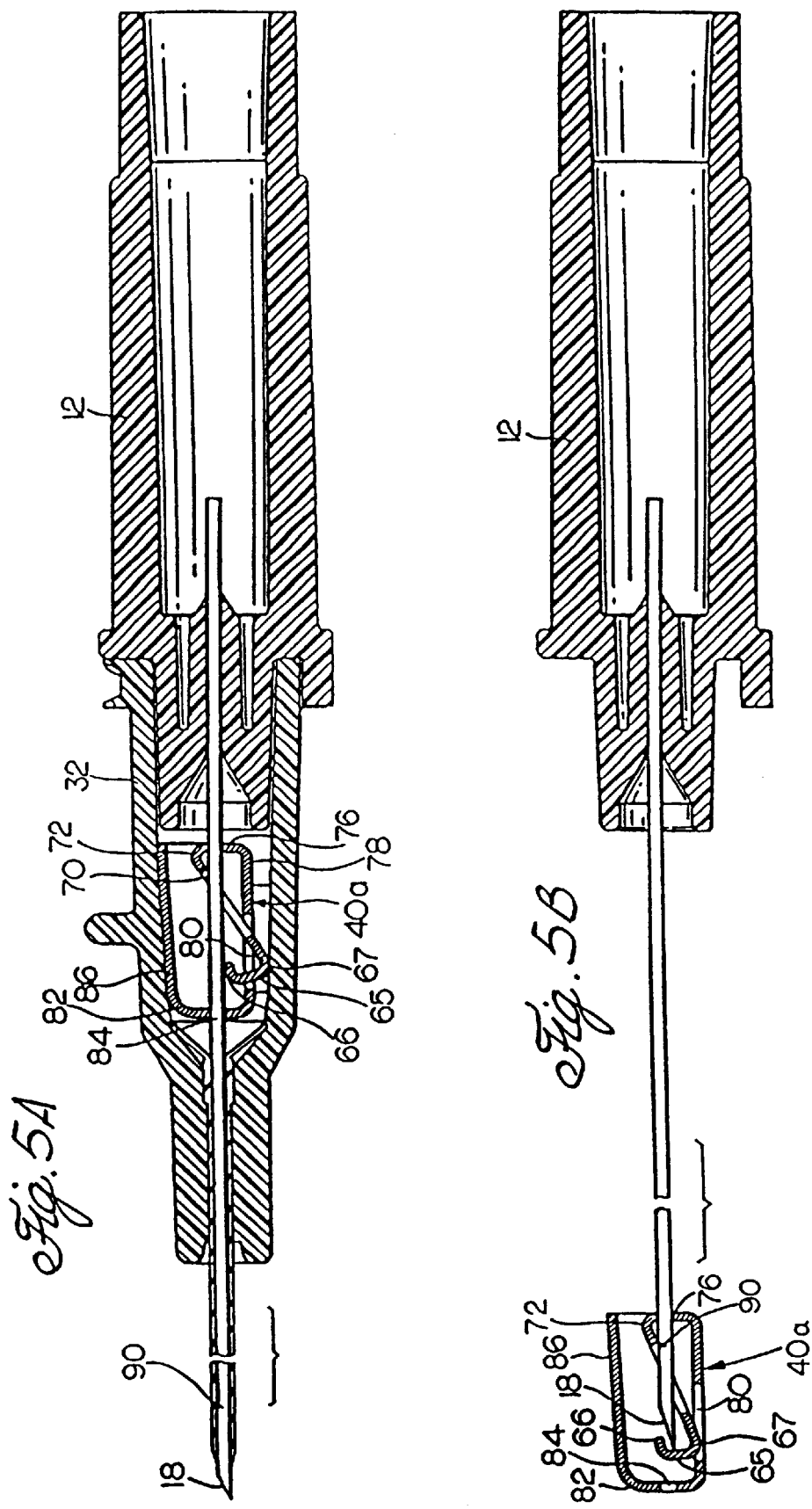

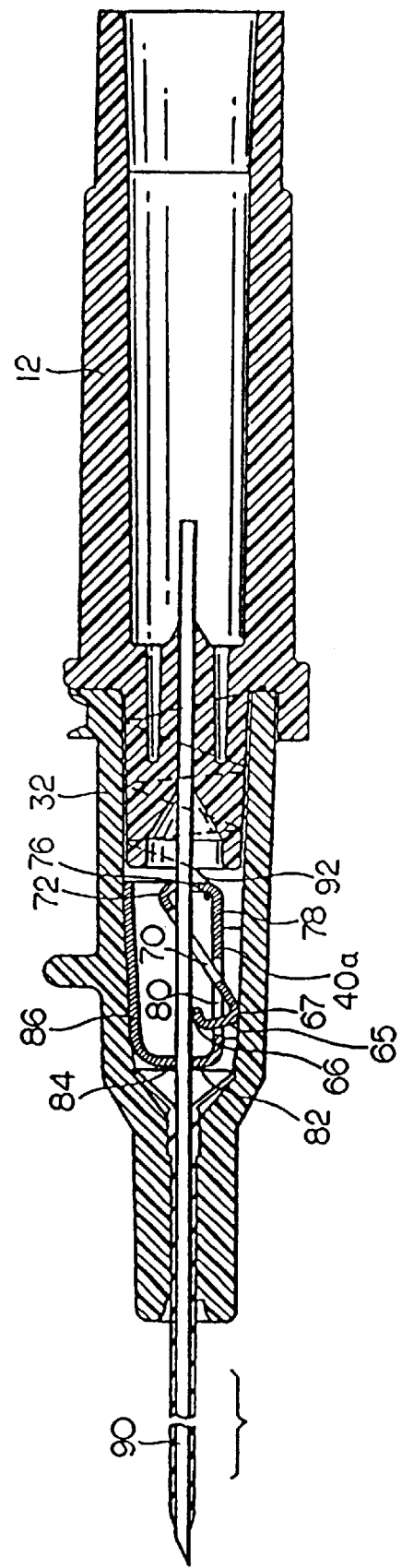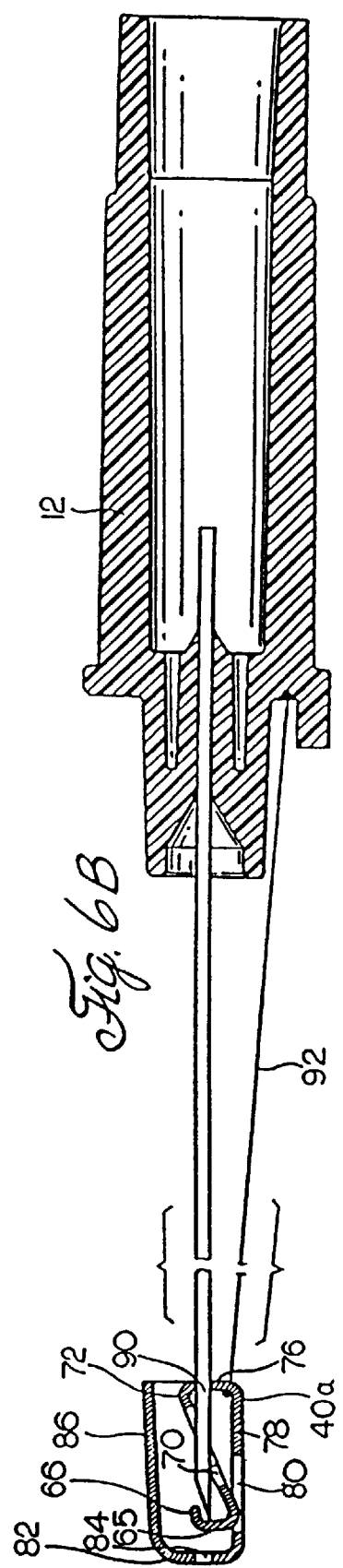

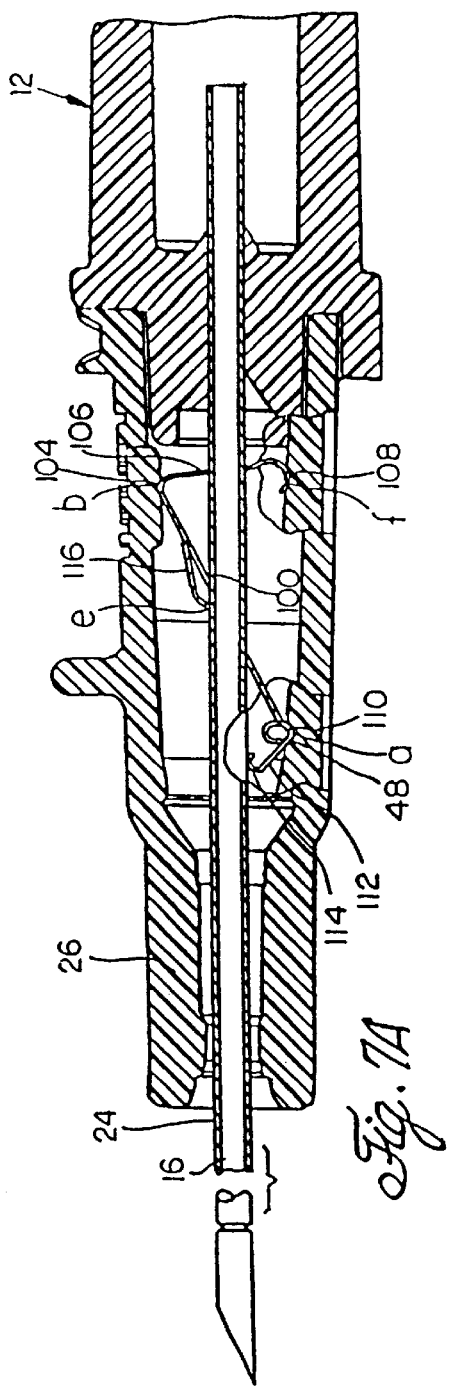
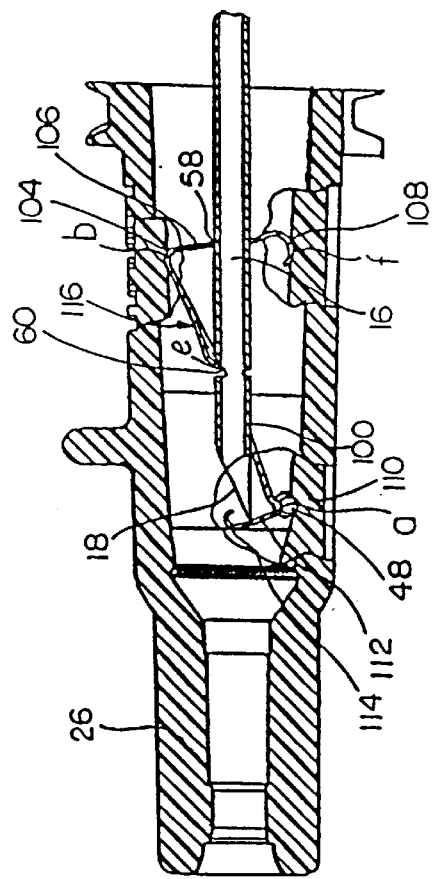
Fig. 7A
Fig. 7B

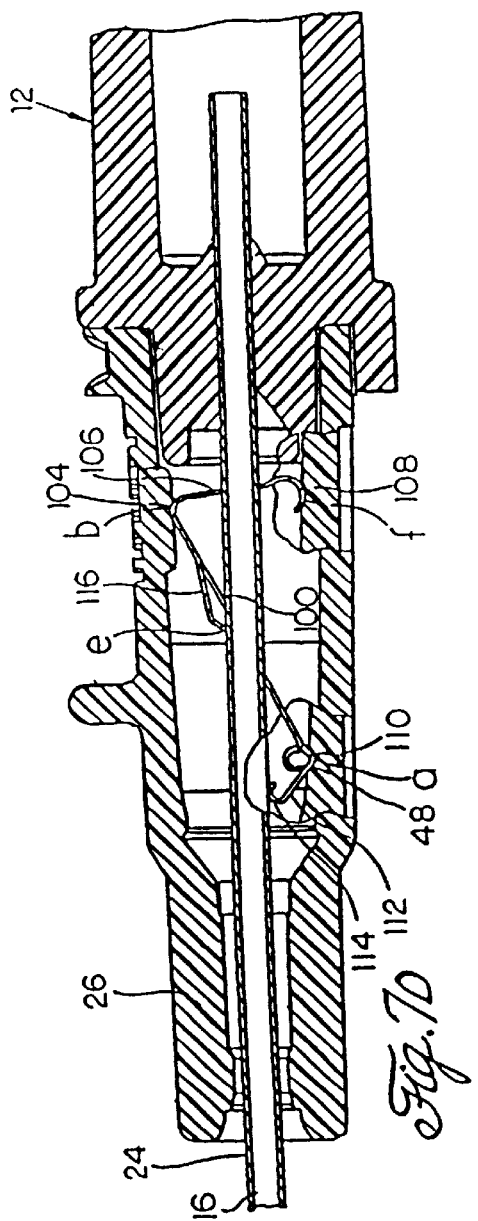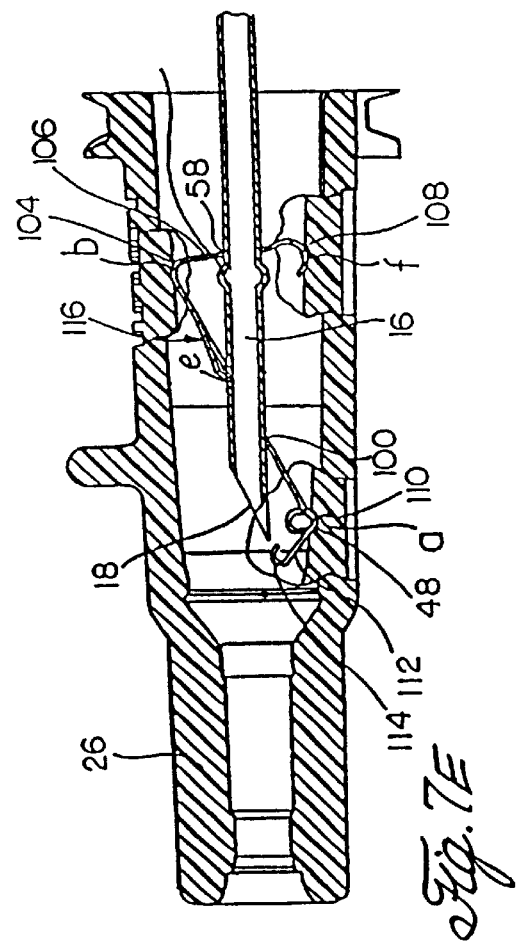

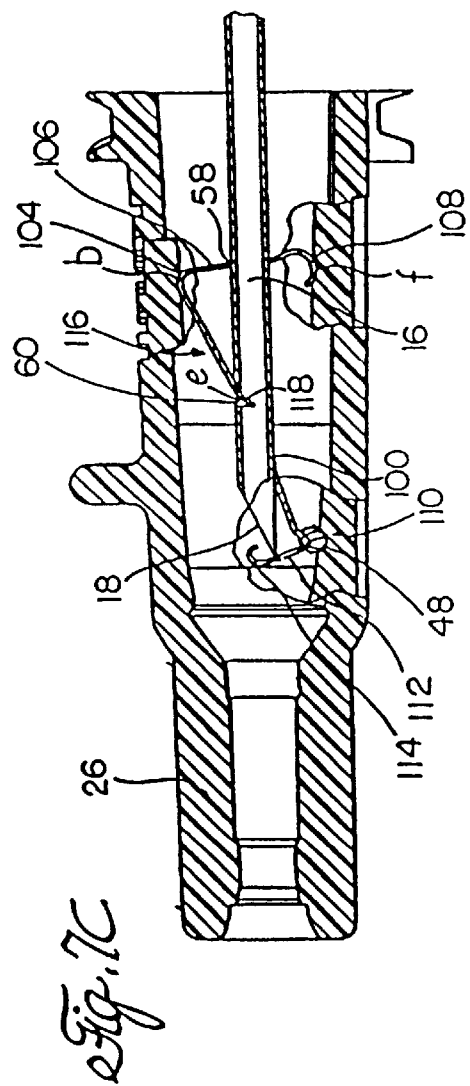
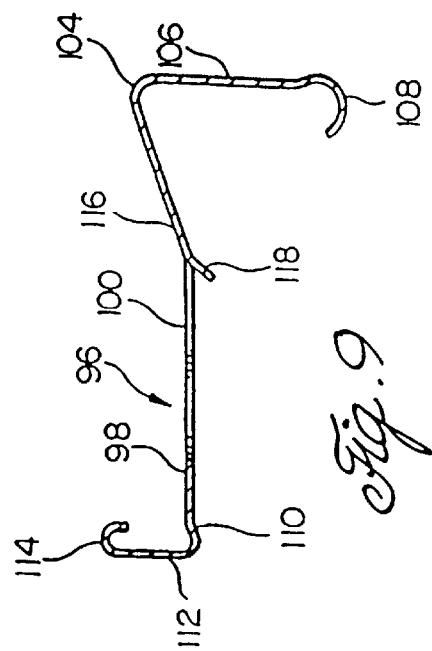
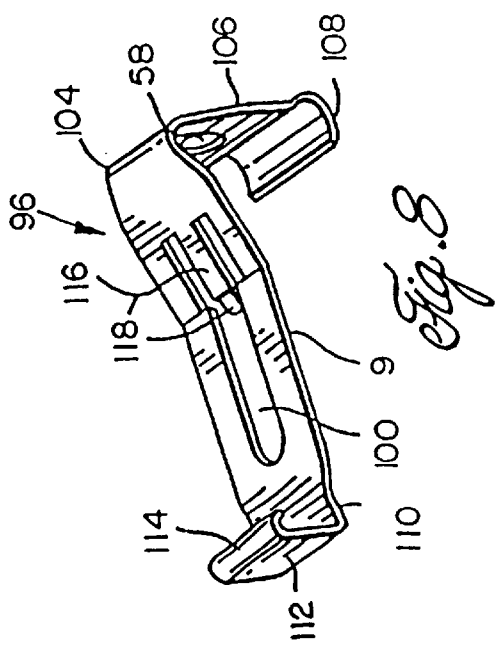

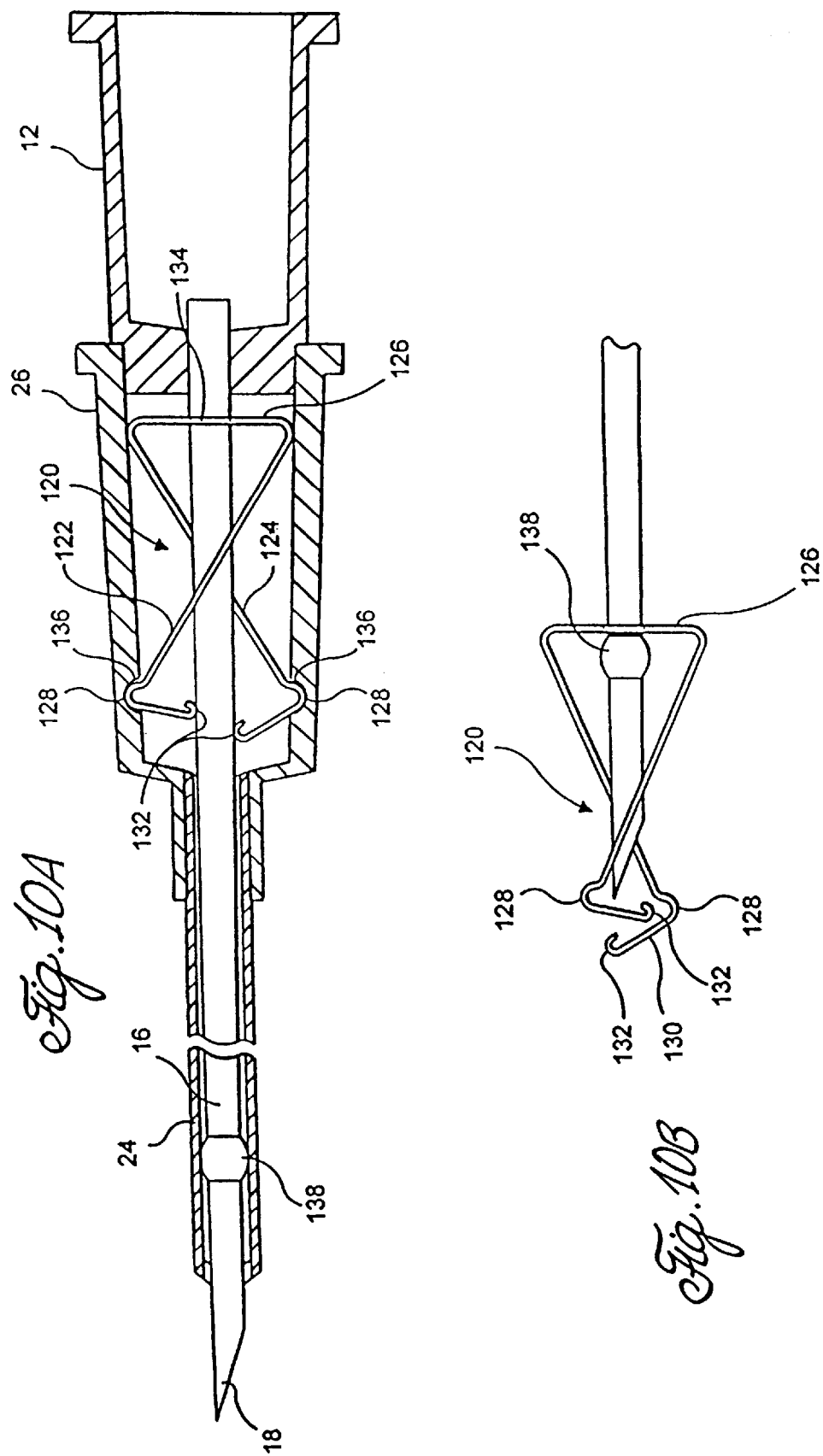

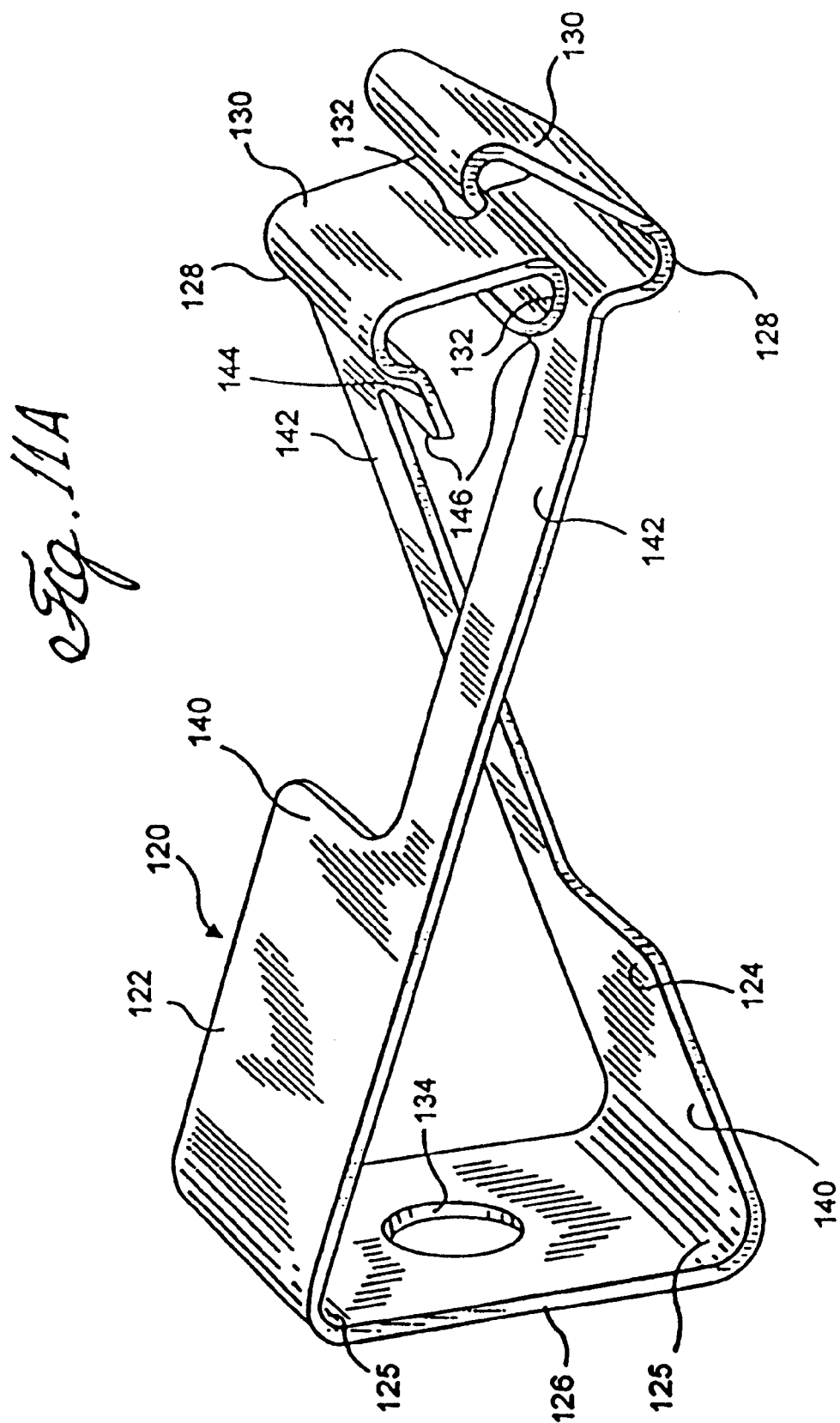

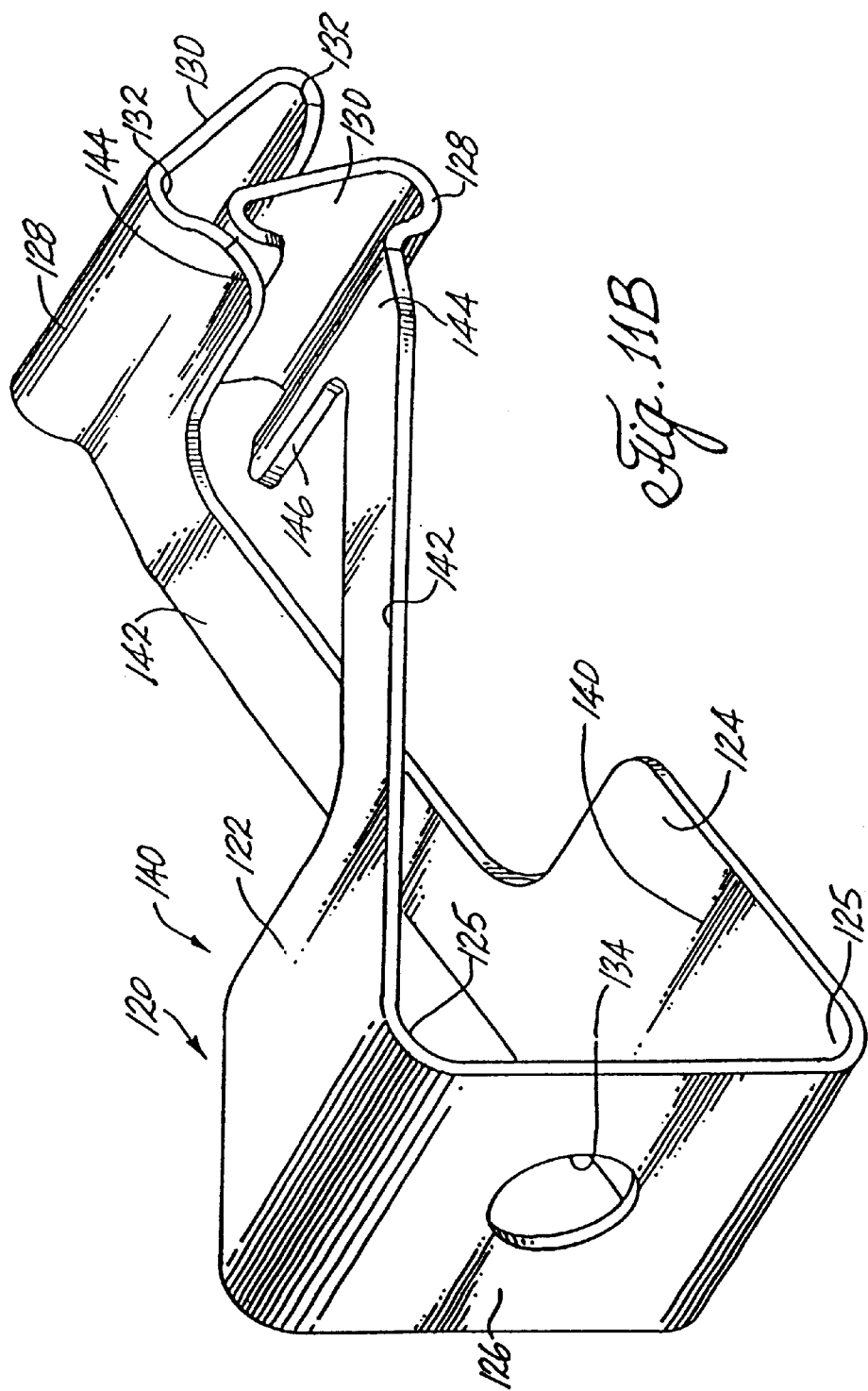

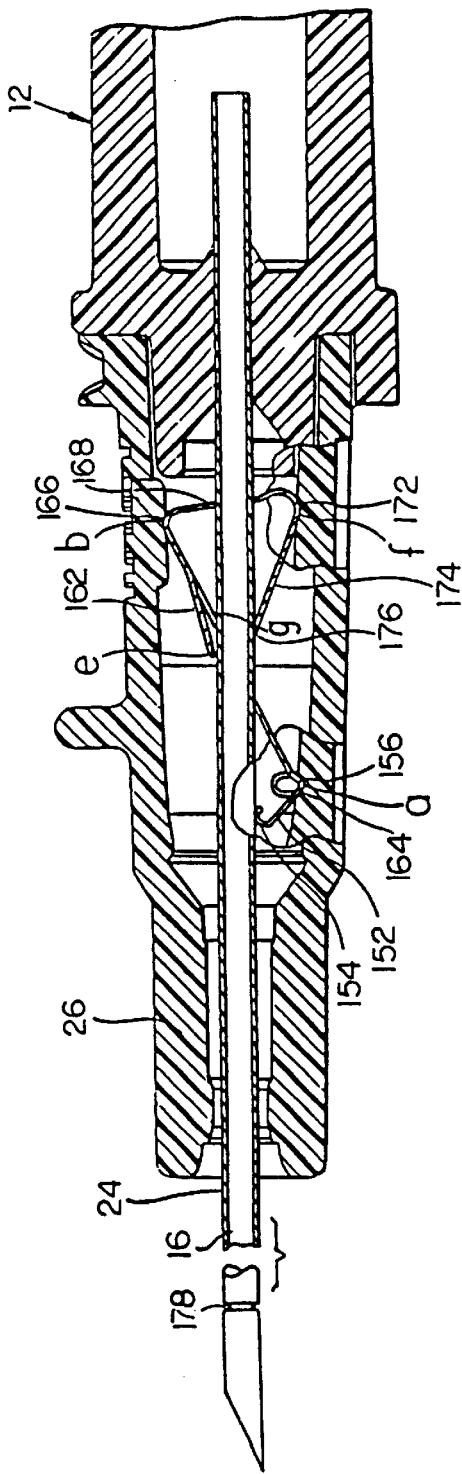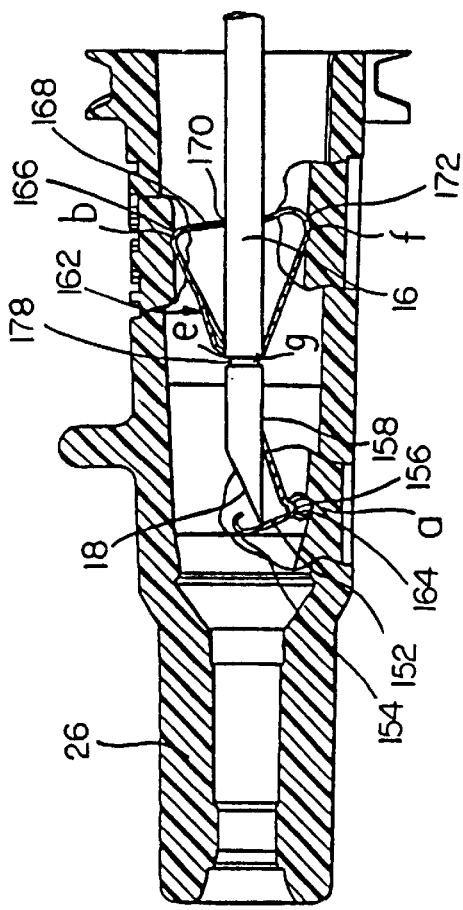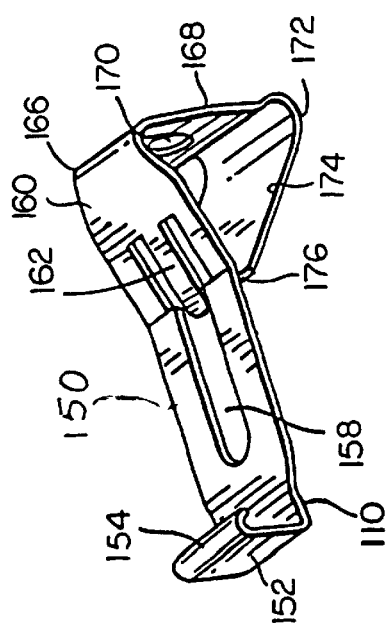

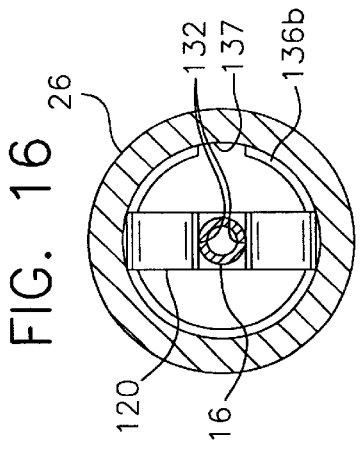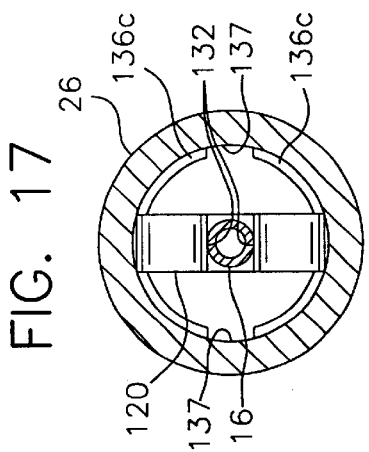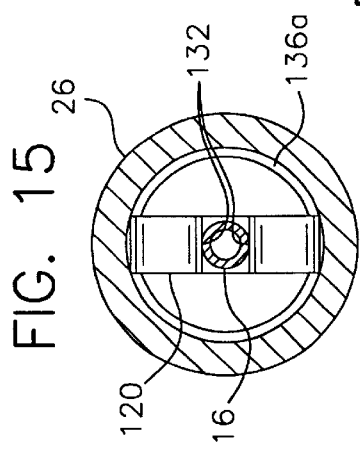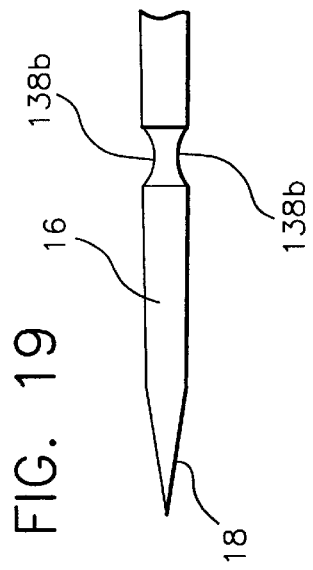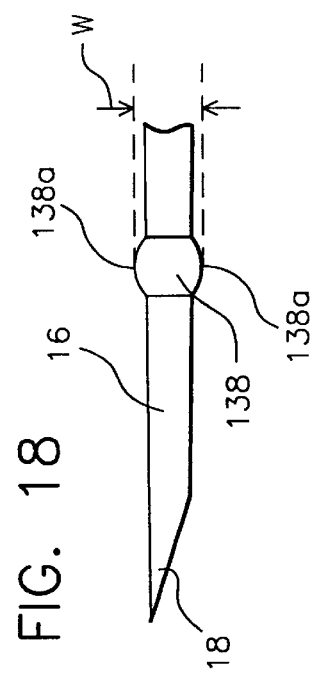

SPRING CLIP SAFETY IV CATHETER

CROSS-REFERENCE TO RELATED APPLICATIONS

This is a continuation-in-part of U.S. Pat. No. 6,287,278, filed Oct. 30, 1998, which is a continuation-in-part of U.S. Pat. No. 6,117,108, filed Jun. 12, 1998, now which is a continuation-in-part of Application Ser. No. 08/915,148, filed Aug. 20, 1997 abandoned, the entire contents of each of which is hereby expressly incorporated by reference.

FIELD OF THE INVENTION

This invention relates generally to intravenous (IV) catheters, and, in particular, to a safety IV catheter in which the needle tip is automatically covered after needle withdrawal to prevent the healthcare worker from making accidental contact with the needle tip.

BACKGROUND OF THE INVENTION

IV catheters are primarily used to administer fluids, sometimes containing medications, directly into a patient's vascular system. The catheter is inserted into a patient's vein by a healthcare worker by using a handheld placement device that includes a sharp tip needle. The needle is positioned in the interior hollow portion of the catheter with its tip extended slightly beyond the edge of the catheter. The end of the apparatus opposite the needle tip is made up of the needle connected to a needle hub which is capable of being held by the healthcare worker during the insertion procedure.

The insertion procedure contains four basic steps: (1) the healthcare worker inserts the needle and catheter together into the patient's vein; (2) after insertion into the vein with the needle point, the catheter is forwarded into the vein of the patient by the healthcare worker pushing the catheter with his or her finger; (3) the healthcare worker withdraws the needle by grasping the hub end (opposite the point end) while at the same time applying pressure to the patient's skin at the insertion site with his or her free hand; and (4) the healthcare worker then tapes the now inserted catheter to the patient's skin and connects the exposed end of the catheter (the catheter hub) to the source of the fluid to be administered into the patient's vein.

The problem is that, immediately after the withdrawal of the needle from the patient's vein, the healthcare worker, who is at this time involved in at least two urgent procedures, must place the exposed needle tip at a nearby location and address the tasks required to accomplish the needle withdrawal. It is at this juncture that the exposed needle tip creates a danger of an accidental needle stick occurring, which, under the circumstances, leaves the healthcare worker vulnerable to the transmission of various dangerous blood-borne pathogens, including AIDS and hepatitis.

This danger to the healthcare worker from accidental needle sticks has caused an impetus for the development of a safer IV catheter in which the occurrence of such accidental needle sticks is prevented. Safety catheters that have been developed to achieve this result are disclosed, for example, in Lemieux Reissue U.S. Pat. No. Re. 34,416, Crawford U.S. Pat. No. 5,558,651, McLees U.S. Pat. No. 5,135,504, Gaba U.S. Pat. No. 5,697,907, and Dombrowski U.S. Pat. No. 4,978,344. Kulli U.S. Pat. No. 4,929,241 and Chamuel U.S. Pat. No. 5,053,107 disclose a protective needle guard for use with a hypodermic needle.

The prior art safety catheters all exhibit one or more drawbacks that have thus far limited their usefulness and full acceptance by healthcare workers. For example, in the safety catheter disclosed in the Lemieux patent, the force required to engage the needle slot within the guard flange is relatively great and would interfere with the removal of the needle. Reducing this force to a more acceptable level would create the possibility of the needle guard remaining in the catheter hub after the needle is removed from the catheter. As a result, the safety catheter disclosed in the Lemieux patent would not consistently function in a reliable manner.

Similarly, the user of the safety catheter disclosed in the Dombrowski patent would have to exert a considerable force to remove the protective cap from the catheter hub when the cap engages a needle. The safety catheter disclosed in the Dombrowski patent would also be relatively expensive to fabricate because of its inclusion of a flexible flange and a tether.

The McLees protective device requires an irksome extra pulling action or tug on the needle guard through a retention ring to remove the protected needle from the catheter hub. The McLees device also requires the assembly of two separate components and is thus relatively costly to manufacture. In addition, the needle in the McLees device includes a larger diameter portion near and at the needle tip. This feature of the McLees device would require that the remainder of the needle be of a lesser diameter which would have the adverse effect of slowing the blood flashback through the needle.

SUMMARY OF THE INVENTION

It is accordingly an object of the present invention to provide a safety IV catheter which reliably and automatically prevents accidental, inadvertent contact with the needle tip after use.

It is a further object of the invention to provide a safety catheter which provides reliable protection to the healthcare practitioner against needle sticks without requiring any change in the manner of use of the safety catheter by the practitioner.

It is another object of the present invention to provide a safety IV catheter of the type described which is relatively simple and inexpensive to manufacture.

It is yet a further object of the present invention to provide a safety catheter of the type described in which removal of the needle from the needle guard after use is prevented.

To these ends, the safety IV catheter of the invention includes a resilient spring clip needle guard that includes a distal or front end and a proximal or rear wall. The spring clip is inserted into the catheter hub and is urged by the needle shaft into contact with the inner walls of the catheter hub so that the needle guard is reliably retained therein. When the needle is withdrawn from the catheter, the force it had previously exerted on the needle guard is released, causing the needle guard to pivot within the catheter hub until it clamps onto the needle shaft. At this time, the distal end wall of the needle guard blocks the distal pointed end tip of the needle. In addition, the spring clip and protected needle onto which it is clamped can be readily and safely removed from the catheter hub. The needle may be provided with a slot or, alternatively, may be provided with a segment of increased width, such as a crimp, which cooperates with the needle guard to prevent the inadvertent removal of the needle from the needle guard after their removal from the catheter hub.

In another embodiment, an IV catheter apparatus is provided which comprises a tubular catheter having a proximal end and a distal end and a needle having a needle shaft and a tip, where the needle is received within the tubular catheter when in a ready position. A catheter hub is attached to the proximal end of the catheter, where the catheter hub has a hollow interior and an inner wall. The needle is movable between the ready position, in which the tip is outside of the catheter hub, and a retracted position, in which the tip is within the interior of the catheter hub. A unitary needle guard is positioned in the interior of the catheter hub and includes a resilient portion engaged by the needle shaft when the needle is in its ready position. A section of the resilient portion of the needle guard is urged by the needle shaft into contact with an interior wall of the catheter hub when the needle is in its ready position. An inwardly extending annular protrusion is formed on the interior wall of the catheter hub for engaging a segment of the needle guard for retaining the needle guard in the catheter hub during the movement of the needle between its ready position and its retracted position. The needle guard includes a distal wall extending from the resilient portion and spaced from the needle tip when the needle is in its ready position and movable within the interior of the catheter hub to a blocking position distal of the needle tip when the needle is in its retracted position in which the needle shaft no longer exerts a force on the resilient portion of the needle guard, such that contact between the segment of the needle guard and the catheter hub is released.

In another embodiment of the spring clip safety catheter of the invention, a retaining groove or bump is formed in the inner wall of the catheter hub, which, in the ready position, engages a lower arm of the spring clip to aid in the retention of the spring clip in the catheter hub.

In yet a further embodiment of the spring clip safety catheter of the invention, a slot is formed in the needle. After the spring clip has pivoted to its retracted position and the needle is clamped by the spring clip, further movement of the needle in the proximal direction will cause the rear or proximal arm of the spring clip to seat in the slot, thereby to more securely clamp the needle shaft to the spring clip.

In a further embodiment of the spring clip catheter guard of the invention, a tether is connected to the needle hub and the spring clip guard to prevent the spring clip guard from being pulled off the protected needle without requiring an excessive clamping force therebetween.

In yet a further embodiment of the invention, the spring clip needle guard is in the form of resilient intersecting arms, each terminating at a distal guard wall. When the needle is in the ready position, it passes through the guard and urges the resilient arms away from each other and against the inner wall of the catheter hub. When the needle is retracted past the guard walls, the resilient arms spring to the safety position in which both of the guard walls are positioned distally from the needle tip, thereby to form a barrier that prevents inadvertent contact with the needle tip.

To the accomplishment of the above, and to such further objects as may hereinabove appear, the present invention relates to a safety IV catheter as described with respect to presently preferred embodiments in the following specification, as considered with the accompanying drawings.

BRIEF DESCRIPTION OF THE DRAWINGS

FIGS. 1A and 1B are semi-schematic views in partial cross-section of a safety IV catheter in accordance with a first embodiment of the invention in the ready and retracted positions, respectively;

FIGS. 1C and 1D are semi-schematic views similar to FIGS. 1A and 1B of a possible variation to the embodiment illustrated therein;

FIGS. 2A and 2B are semi-schematic views in partial cross-section of a safety IV catheter in accordance with a second embodiment of the invention in the ready and retracted positions, respectively;

FIGS. 3A and 3B are semi-schematic views in partial cross-section of a safety IV catheter in accordance with a third embodiment of the invention in the ready and retracted positions, respectively;

FIGS. 4A and 4B are semi-schematic views in partial cross-section of a safety IV catheter in accordance with a fourth embodiment of the invention in the ready and retracted positions, respectively;

FIGS. 5A and 5B are semi-schematic views in partial cross-section of a safety IV catheter in accordance with a fifth embodiment of the invention in the ready and retracted positions, respectively;

FIGS. 6A and 6B are semi-schematic views in partial cross-section of a safety IV catheter in accordance with a sixth embodiment of the invention in the ready and retracted positions, respectively;

FIGS. 7A, 7B and 7C are views in partial cross-section of a safety IV catheter in accordance with a further embodiment of the invention in the ready, engaged and retracted or protected positions, respectively;

FIGS. 7D and 7E are semi-schematic views similar to FIGS. 7A and 7B of a possible variation to the embodiment of the invention illustrated therein;

FIG. 8 is a semi-schematic perspective of the spring clip needle guard used in the embodiment of FIG. 7;

FIG. 9 is a semi-schematic cross-section of the spring clip needle guard of FIG. 8;

FIGS. 10A and 10B are semi-schematic views in partial cross-section of a safety IV catheter in accordance with still a further embodiment of the invention shown in the ready and protected positions, respectively;

FIG. 11A and 11B are semi-schematic perspectives of the needle guard clip of the embodiment of FIG. 10;

FIG. 12 is a semi-schematic perspective view of a safety IV catheter in accordance with another embodiment of the invention;

FIGS. 13A and 13B are semi-schematic cross-sectional views of the embodiment of the invention of FIG. 12 in the ready and protected positions, respectively;

FIG. 15 is a semi-schematic cross-sectional view taken along line 15 of FIG. 14, showing a continuous generally annular protrusion;

FIG. 16 is a semi-schematic cross-sectional view similar to that of FIG. 15, showing a generally annular protrusion having a small discontinuity formed therein;

FIG. 17 is a semi-schematic cross-sectional view similar to that of FIG. 15, showing a two-part annular protrusion;

FIG. 18 is a semi-schematic side view of the needle of FIG. 14;

FIG. 19 is a semi-schematic side view of the needle of FIG. 18 rotated 90° about its longitudinal axis;

DETAILED DESCRIPTION OF THE INVENTION

Figure 14:
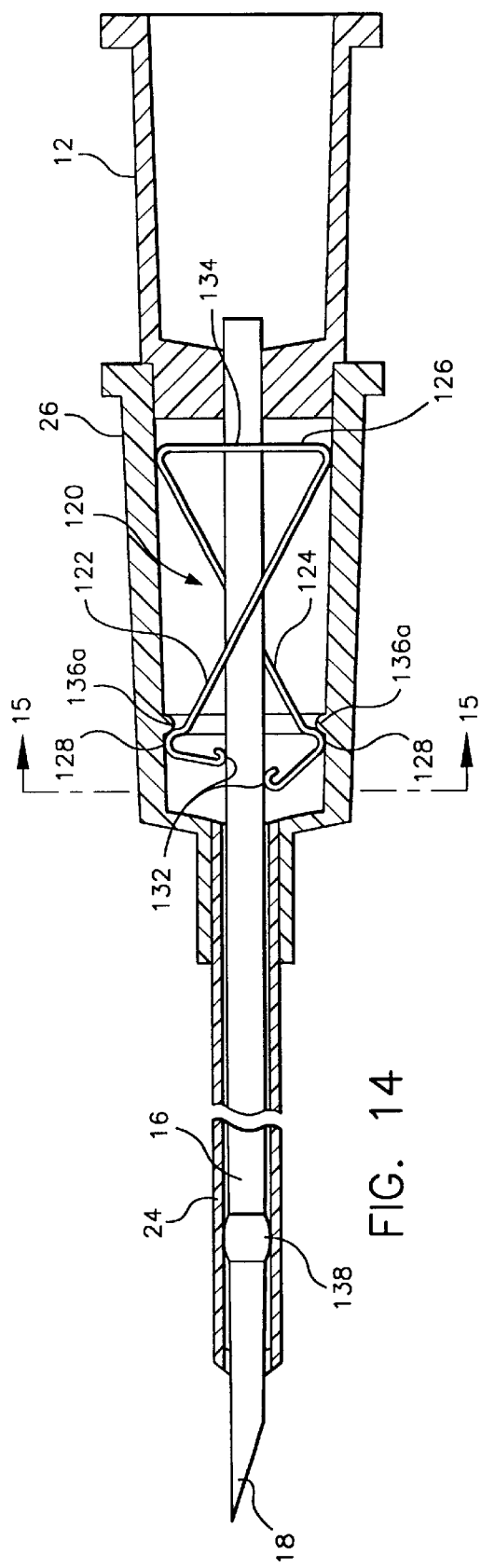
FIG. 14 is a semi-schematic view in partial cross-section of a safety IV catheter in accordance with still a further embodiment of the invention, wherein an inwardly extending annular protrusion is provided to releasably retain the needle guard within the catheter hub.

The safety IV catheter of the invention, generally designated 10 in the embodiment illustrated in FIGS. 1A and 1B, includes a needle hub 12 that includes an axial opening 14 which securely receives the proximal end of a needle 16 having a sharpened tip 18. The needle hub 12, as is conventional, is hollow and includes a flash chamber 22. As is also conventional, the needle 16 is received within a hollow tubular catheter 24, the proximal end of which is concentrically affixed within the distal end of a catheter hub 26 having a distal section 28 and a contiguous, larger diameter proximal section 30.

The catheter hub 26 terminates at its proximal end in a Luer fitting 32 adapted to receive a tubing set which, in a known manner, administers intravenous fluid into the patient. The catheter 24 is secured within an axial passageway 34 in the distal hub section 28 by means of a sleeve 20 received within the passageway 34, which engages the proximal end of the catheter. Passageway 34 communicates at its proximal end with a flash chamber 36 formed in the hub section 30.

In the ready position of the catheter, shown in FIG. 1A, the distal end of the needle hub 12 is snugly received in the proximal end of the interior of the chamber 36 such that the needle 16 extends through the chamber 36, the passageway 34, and distally beyond the catheter hub 26 and catheter 24, so that its tip extends beyond the tapered distal end of the catheter.

In use, the distal tip of the needle and the catheter are inserted into a patient's vein. Thereafter, the healthcare practitioner manually places the catheter further into the vein and then withdraws the needle by grasping and moving by hand the proximal end of the needle hub 12. The Luer of the catheter hub 26 is then fitted with a source of the fluid that is to be administered into the patient's vein.

In accordance with the present invention, as the needle 16 is being withdrawn from the patient, a protective needle guard 40 located within the hub chamber 36 automatically snaps into a retracted position in which it blocks access to the distal needle tip and prevents further distal movement of the needle tip, thereby to prevent accidental contact by the healthcare practitioner with the needle tip.

As shown in FIGS. 1A and 1B, the needle guard 40 is in the form of a unitary spring clip that is preferably made of a resilient metal such as stainless steel. The spring clip includes a distal arm 42 terminating at its upper end in a curved lip 44 and at its lower end in a pointed end 46 which, in the embodiment of FIG. 1, is received within a mating groove 48 formed in the lower interior wall of the catheter hub section 30.

The spring clip needle guard 40 further includes a transverse segment 50 that extends upward and proximally from the lower pointed end 46 and terminates at a U-shaped upper end 52. In the ready position of the spring clip shown in FIG. 1A, the upper end 52 abuts against the upper interior wall of the catheter hub section 30. The spring clip guard 40 further includes a vertical arm 54 that extends downward from the U-shaped upper end 52 and terminates above the lower wall of the catheter hub section 30. The transverse segment 50 and proximal vertical arm 54, respectively, include axially aligned openings 56, 58 through which the shaft of the needle 16 is free to pass and axially move. The diameter of the opening 58 is slightly greater than that of the needle shaft, whereas the diameter of the opening 56 is greater than that of the opening 58.

In the ready position of the catheter prior to needle withdrawal, the shaft of the needle 16 engages the curved lip 44 of the spring clip needle guard 40, thereby to exert an essentially downward force on the resilient spring clip. That force causes the lower end 46 of the spring clip to seat securely in the groove 48 at point A. That contact, in addition to the abutment of the upper end 52 of the spring clip with the upper interior wall at the catheter hub at point B, securely maintains the spring clip needle guard 40 in the ready position within the catheter hub.

As the needle 16 is retracted to the left, as viewed in FIG. 1A, to its fully retracted position, shown in FIG. 1B, after catheter insertion into the patient's vein, the distal tip of the needle moves proximally past the curved lip 44 of the spring clip needle guard 40 at point C, at which time the downward force previously exerted by the needle shaft on the spring clip is released.

As a result of the needle 16 moving proximally past point C, the retention force on the spring clip needle guard 40 in the catheter hub is released, causing the spring clip needle guard 40 to pivot or snap in a clockwise direction to the retracted position shown in FIG. 1B. As therein shown, distal arm 42 of the needle guard 40 blocks the distal path of the needle 16. Simultaneously with the blocking and releasing actions, the spring clip guard 40 becomes securely clamped onto the needle shaft at points D and E, thereby to securely lock the needle guard 40 onto the needle shaft. At this time, the needle 16 and needle guard 40 can be removed together from the catheter hub 26, and the tip of the needle cannot be pushed past the needle guard because it is blocked by the distal arm 42 and lip 44 of the needle guard.

If desired, a slot 60 may be formed in the needle shaft slightly proximal to the needle tip. When the needle and the needle guard are in their retracted and clamped positions (FIG. 1B), slot 60 is positioned slightly distal to the clamping point E of the transverse segment of the needle guard 40 such that if a subsequent attempt is made to move the needle further in a rearward or proximal direction, the transverse segment 50 at point E will seat into slot 60, thereby to provide an additional force to retain the needle guard 40 on the needle 16 in the protected position in which access to the needle tip is prevented.

The safety IV catheter illustrated in FIGS. 1C and 1D is the same as that illustrated in FIGS. 1A and 1B, except that the slot 60 in the needle shaft in the latter is replaced in the former by a crimp 61 whose width is greater than that of the opening 58 in the vertical arm 54. If an attempt is made to move the protected needle illustrated in FIG. 1C in the rearward or proximal direction, the crimp 61 will engage the wall 54 and will thus not be able to pass through the opening 58, so as to prevent further proximal movement of the needle and removal of the needle from the needle guard, as defined.

The embodiment of the invention illustrated in FIG. 2 is similar to that of FIG. 1 except that, instead of the groove formed in the lower wall of the catheter hub that engages the lower end of the spring clip, a retaining bump 62 is formed in that wall against which the lower end 46 of the needle guard 42 seats when the needle guard 40 is in the ready position, as shown in FIG. 2A.

The embodiment of the invention illustrated in FIGS. 3A and 3B is essentially the same as that of FIG. 2 with the addition of a tether 64 secured at one end to the needle hub 12 and at its other end to the proximal arm 54 of the spring clip needle guard 40. As shown in FIG. 3B, the tether 64 is extended to its full length when the needle hub is retracted to achieve needle removal, so as to more securely retain the needle hub 12 and the spring clip needle guard 40 when the latter is clamped onto the needle when in the retracted position in which, as described above, the distal arm 42 of the spring clip prevents access to the needle tip, and the needle guard 40 and needle are released from the catheter hub.

FIGS. 4A and 4B illustrate a spring clip needle guard embodying the principles of the invention in an alternative configuration. As therein shown, the spring clip needle guard 40a includes a distal arm 65 terminating at its upper end in a curved lip 66 and at its lower end in a U-shaped portion 67 which, in the ready position illustrated in FIG. 4A, contacts a bump 68 formed in the lower inner wall of the catheter hub.

A transverse segment 69 having a central opening 70 extends proximally and upwardly and terminates at an upper U-shaped portion 72. A proximal end wall 74 having an opening 76 depends vertically from portion 72 and then extends distally in a horizontal lower segment 78 which has an opening 80 through which the lower halves of the distal arm 65 and the transverse segment 69 extend in the ready position of the needle guard. Segment 78, at its distal end, extends upwardly at a front wall 82 which has a central opening 84 axially aligned with openings 70, 76. At its upper end, the distal front wall 82 extends in the proximal direction in an upper segment 86 which, as shown in FIG. 4A, contacts the upper inner wall of the catheter hub along substantially its entire length.

As shown in FIG. 4A, when the catheter is in the ready position, the needle shaft passes through openings 70, 76 and 84 and rests on the curved lip 66, urging the arm 65 against the bump 68 in the lower wall of the catheter hub. That engagement, along with the resilient engagement of the upper segment 86 with the upper interior wall of the catheter hub, retains the spring clip 40a in its ready position within the catheter hub.

When the needle hub and needle are retracted to the right, as viewed in FIG. 4A, by a sufficient amount, the needle tip passes below the lip 66 and then releases its downward force on the arm 65. As described above with reference to the first-described embodiment, this release of engagement of the needle shaft and the spring clip arm 65 causes the arm 65 to snap upwards to the retracted position illustrated in FIG. 4B, in which the arm 65 and the lip 66 extend over the needle tip and thereby prevent accidental contact with the needle tip as desired. In this condition, the needle guard is clamped onto the needle shaft in essentially the same manner described above with respect to the first-described embodiment, and the needle and needle guard clamped thereto can be readily removed from the catheter hub, also as described above and as shown in FIG. 4B.

The embodiment of the needle guard illustrated in FIGS. 5A and 5B is essentially the same as that shown in FIGS. 4A and 4B, with the addition of a slot 90 near the distal tip end of the needle. When the needle and needle guard are in their retracted and clamped position (FIG. 5B), the slot 90 is positioned slightly distal to the clamping point of the transverse segment 69 such that if a subsequent attempt is made to move the needle further in a rearward or proximal direction, the transverse segment 69 will seat into the slot 90, thereby to provide an additional force to retain the needle guard in the needle in the protected position in which access to the needle tip is prevented.

The embodiment of the invention illustrated in FIGS. 6A and 6B is the same as that illustrated in FIGS. 4A and 4B, except for the inclusion of a tether 92 secured at one end to the needle hub and at its other end to the proximal wall of the spring clip needle guard. As shown in FIG. 6A, in the ready position, the tether is wound around the distal end of the needle hub. As shown in FIG. 6B, when the needle and needle guard are in their retracted position, the tether is extended to its full length and aids in the retention of the needle guard to the needle hub. If desired, the embodiment of the invention embodiment illustrated in FIGS. 6A and 6B could also include a needle slot as in the embodiment of the invention illustrated in FIGS. 5A and 5B.

The embodiment of FIGS. 7A–7C differs from the previously described embodiments primarily with regard to the construction and operation of the spring clip needle guard 96. As shown in FIGS. 8 and 9, the spring clip 96 includes a central transverse section 98 which includes a central slot 100. A sloping section 102 extends from section 98 in the proximal direction and terminates at a curved end 104 from which a proximal vertical arm 106 extends. The arm 106 terminates at its lower end in a U-shaped section 108. The distal end of the transverse section 98 terminates in a curved section 110 from which a vertical proximal arm 112 extends. The distal arm 112 terminates at its upper end in a curved arm 114.

A cutout portion in section 98 defines a flexible flap 116 which terminates at its distal free end in a downwardly sloping locking tab 18. As in the prior embodiments, the proximal arm 106 includes an opening 58.

As shown in FIG. 7A, the spring clip needle guard 96, when in the ready position illustrated therein, is inserted within the catheter hub 26 so as to allow the needle 16 to pass through the opening 58 and slot 100. As in the previously described embodiments, the curved end 104 abuts against the inner upper wall of the catheter hub 26 at point B, and the curved section 110 seats within the mating groove 48 at point A formed in the lower inner wall of the catheter hub. In addition, the lower curved section 108 contacts at point F the lower inner wall of the catheter hub 26 at a location proximal to point B.

In operation, the needle is initially withdrawn into the catheter hub until it reaches the tab engaged position illustrated in FIG. 7B in which, as therein shown, the locking tab 118 is received within the needle groove or slot 60. At this point, the spring clip remains in contact with the inner wall of the catheter hub at points A, B and F, while the needle tip 18 engages the curved end 114, thereby to urge section 110 into the groove 48 at point C. The relative position of point F with respect to point B prevents the needle and clip from being prematurely released from the catheter hub by preventing the distal end of the clip from tipping upwards and the proximal end from slipping downward with the clip in the tab engaged position shown in FIG. 7B.

As the needle is withdrawn further away from the patient, as shown in FIG. 7C, the needle tip passes beyond the curved end 114, thereby releasing the downward force that had been previously exerted on the curved end 114 by the needle.

This sudden release of the downward force on the spring clip end causes the distal end of the spring clip 96 to pivot upward so that the distal end 112 of the spring clip 96 moves rapidly to a position in which it prevents or blocks the motion of the needle in the distal direction. The spring clip 96 is retained on the needle 16 and will be removed from the catheter hub 26 when the needle is completely removed. Movement of the spring clip 96 from its protecting or retracted position shown in FIG. 7C is further prevented by the insertion of the locking tab 118 into the needle groove 60, which prevents the spring clip from rotating around the periphery of the needle. This, in turn, secures the spring clip on the needle, even if the clip were subjected to a twisting and pulling force.

The safety IV catheter illustrated in FIGS. 7D and 7E is the same s that illustrated in FIGS. 7A and 7B, except that the slot 60 in the needle shaft in the latter is replaced in the former by a crimp 61 whose width is greater than that of the opening 58 in the vertical arm 54. If an attempt is made to move the protected needle illustrated in FIG. 7D in the rearward or proximal direction, the crimp 61 will engage the wall 54 and will not be able to pass through the opening 58, so as to prevent any further proximal movement of the needle and removal of the needle from the needle, as desired.

The embodiment of the spring clip needle guard 120 disclosed in FIGS. 10A, 10B, and 11 comprises first and second arms 122 and 124, respectively, joined at their proximal ends in a hinged arrangement at 125 to the ends of a rear wall 126. The distal ends of the arms 122, 124 each include a curved protrusion 128 extending to a distal end wall 130, which, in turn, terminates in a lip 132. As seen best in FIG. 11, the rear wall 126 includes a central opening 134, and the arms 122 and 124 each include a narrow portion 142 that extends between a distal wide portion 140 and a proximal wide portion 144. A lateral clamping edge 146 is defined at the distal wide portion 144.

As shown in FIG. 10A, when the needle guard 120 is in its ready position, the curved protrusions 128 in each of the arms 122, 124 are received in an annular groove or ring 136 formed in the inner wall of the catheter hub 26 which, as in the prior embodiments, is removably fit into the distal end of a needle hub 12. Also as in the prior embodiment, a needle 16 having a sharpened tip 18 at its distal end is received within a tubular catheter 24 which is secured t the distal end of the catheter hub 26. The proximal end of the needle 16 passes through the opening 134 in the rear wall 126. The needle 16 includes an crimp 138 which is sufficiently small to allow the needle 16 to move axially along the catheter 24 but is greater in width than the opening 134 for reasons to be described below.

In the ready position illustrated in FIG. 10A, the needle shaft passes through the needle guard and applies an outward radial force on the resilient arms 122, 124 by means of its engagement with the lips 132, so as to urge the curved protrusions 128 of each of the arms into the annular groove 136, so as to retain the needle guard 120 in a fixed position within the inner wall of the catheter hub 26. The shaft of a needle 16 that passes through the needle guard 120 frictionally engages the inner edges of the narrow portion 142 of arms 122, 124 so as to further retain the needle in its ready position.

When the needle is retracted axially to the right, as viewed in FIG. 10A, within the catheter hub and moves past the end lip 132 of the needle guard, the radial force previously exerted on the arms 122, 124 of the needle guard 120 is suddenly released. This causes the distal end walls 130 of the needle guard to be released from their seat in the annular groove 136 and to pivot inward into the catheter hub until, as seen in FIG. 10B, the end walls 130 overlap one another at a location distally in front of the needle tip, thereby to form a barrier that prevents inadvertent contact with, and distal movement of, the needle tip. At the same time, the clamping edges 146 of the needle guard are urged against the needle tip to restrict further axial movement of the needle.

As also shown in FIG. 10B, the needle guard 120 and the needle clamped to the needle guard after needle retraction can be removed from the catheter hub as a unitary assembly and safely discarded. If an attempt is made, intentionally or inadvertently, to pull the needle further to the right, as shown in FIG. 10B, out of the needle guard, the crimp 138 on the needle shaft will come into contact with the end wall 126, and, since its width is greater than that of the opening 134, the end wall 126 will at this point prevent any further axial movement of the needle out of the needle guard.

This spring clip guard of the invention, in the embodiment illustrated in FIGS. 12, 13A and 13B, includes a transverse arm 150 terminating at its distal end at a distal end wall 152, which includes at its upper end a curved lip 154 and at its lower end a curved end 156. An elongated rectangular opening or slot 158 is provided in the transverse arm 150. The proximal ends of the transfer arm 150 and the opening 158 terminate at an extension 160 extending upwardly at an angle from the arm 150 and having a finger or flap 162 that extends toward the opening 158.

The proximal end of the extension 160 terminates t a curved end 166 from which a proximal end wall 168 extends downwardly. The wall 168, which includes an opening 170, terminates at its lower end at a curved section 172 from which extends an upwardly sloping arm 174 that terminates at a clamping edge 176. As can be seen in FIGS. 13A and 13B, a 360° circular groove 178 is formed about the circumferential wall of the needle 16 slightly inwardly from the tip 18 of the needle.

In the ready position of the spring clip guard of FIG. 12, as illustrated in FIG. 13A, the shaft of the needle passes through the aligned opening 170 in the rear wall 168 and the opening 158 in the transverse arm 150 and extends distally beyond the catheter hub. As in the prior embodiments described hereinabove, the needle shaft in this position exerts a downward radial force on the arm 150 by means of its engagement with the curved lip 154. This downward force urges the curved end 156 of the spring clip to seat firmly within a groove 164 formed in the inner wall of the catheter hub at point A.

At the same time, the upper curved end 166 of the end wall 168 engages the inner wall of the catheter hub at point B, and the lower curved end 172 of the wall 168 engages the inner wall of the catheter hub at point F. Further engagement between the needle shaft and the spring clip is provided by the contact of the finger 162 with the upper end of the needle shaft at point E and between the clamping edge 176 and the lower surface of the needle shaft at point G. In this manner, the needle is securely but movably retained within the catheter hub in its ready position.

When the needle is retracted axially to the right, as viewed in FIGS. 13A and 13B, it eventually moves past its engagement with the lip 154, thereby to suddenly release the radial force it had previously exerted on the arm 150 of the needle guard. This release of engagement between the needle shaft and the lip 154 allows the distal curved end 156 of the distal end wall 152 of the spring clip to be released from its seat in the annular groove 164 so that the arm 150 and the end wall 152 pivot quickly into the interior of the catheter hub, as seen in FIG. 13B, to a position at which the wall 152 forms a barrier to the needle tip. This positioning of the wall 15 prevents inadvertent contact with the needle tip. The engagement of the finger 162 and the clamping edge 176 to the opposing sides of the needle prevents further axial movement of the needle in either direction.

If an attempt is thereafter made to pull the needle axially further to the right, as viewed in FIG. 13B, the finger 162 will enter the circular groove 178 formed in the needle surface, thereby to prevent further axial movement of the needle in the proximal direction out of the needle guard.

As shown in FIG. 14, yet a further embodiment of the present invention is generally similar to the embodiment shown in FIG. 10A, with the notable exception that the annular groove or ring 136 of the embodiment shown in FIG. 10A has been replaced with an inwardly extending annular protrusion 136a which serves an analogous function with respect to the annular groove or ring 136. Preferably, the annular protrusion 136a extends completely around the interior of the catheter hub 26 in a generally continuous ring-like fashion.

The annular protrusion 136a removably retains the needle guard 120 within the catheter hub 26 as the needle 16 is withdrawn from the catheter hub 26, until the arms 122, 124 of the needle guard 120 move inwardly as the tip 18 of the needle 16 moves past the end lips 132 of the needle guard 120, as discussed in detail above.

Although the annular protrusion 136a is shown in FIG. 14 as having a generally semi-circular cross-section, those skilled in the art will appreciate that various other cross-sectional configurations of the annular protrusion 136a are likewise suitable. For example, the annular protrusion 136a may alternatively have a generally triangular, square, rectangular, or any other desired cross-sectional configuration.

The annular protrusion 136a is preferably formed integrally with respect to the catheter hub 26, such as being injection molded as a portion thereof. Alternatively, the annular protrusion 136a may be formed separately from the catheter hub 26 and attached to the catheter hub 26 via adhesive bonding, ultrasonic welding or any other desired method.

Moreover, it will be appreciated that the annular protrusion 136a may have any desired configuration which releasably retains the needle guard 120 within the catheter hub 26 until the tip 18 of the needle 16 has been withdrawn past the lips 132 of the needle guard 120.

As shown in FIGS. 14 and 15, when the needle guard 120 is in its ready position, the curved protrusions 128 in each of the arms 122, 124 are positioned near, e.g., in abutting contact with, the annular protrusion 136a formed on the inner wall of the catheter hub 26 which, as in the prior embodiments, is removably fit onto the distal end of a needle hub 12. Also, as in the prior embodiment, a needle 16 having a sharpened tip 18 at its distal end is received within a tubular catheter 24 which is secured to the distal end of the catheter hub 26. The proximal end of the needle 16 passes through the opening 134 in the rear wall 126 of the needle guard 120. The needle 16 includes an crimp 138 which is sufficiently small to allow the needle 16 to move axially along the catheter 24 but which is greater in width than the opening 134 for reasons to be described below.

In the ready position illustrated in FIGS. 14 and 15, the needle shaft passes through the needle guard 120 and applies an outward radial force on the resilient arms 122, 124 by means of its engagement with the lips 132, so as to urge the curved protrusions 128 of each of the arms against the inner wall of the catheter hub 26, so as to retain the needle guard 120 in a fixed position within the catheter hub 26. As was the case with the embodiment described with respect to FIGS. 10A and 10B, the shaft of a needle 16 that passes through the needle guard 120 and optionally frictionally engages the inner edges of the narrow portion 142 (shown in FIG. 11) of arms 122, 124 so as to further retain the needle in its ready position.

When the needle is retracted axially to the right, as viewed in FIG. 14, and moves past the end lips 132 of the needle guard 120, the radial force previously exerted on the needle guard arms 122, 124 is suddenly released. The annular protrusion 136a prohibits movement of the needle guard 120 to the right as the needle 16 moves to the right, until the tip 18 past the end lips 132 of the needle guard 120. Movement of the tip 18 past the end lips 132 allows the resilient arms 122, 124 and their protrusions 128 therein to move inwardly a sufficient distance to cease abutting the annular protrusion 136a. As was the case with the embodiment described with regard to FIGS. 10A and 10B, the distal end walls pivot inward into the catheter hub until the end walls overlap one another at a location distally in front of the needle tip, thereby to form a barrier that prevents inadvertent contact with, and distal movement of, the sharpened needle tip 18. At the same time, the clamping edges 146 of the needle guard (as described with respect to FIG. 11) are optionally urged against the needle 16 to restrict further axial movement of the needle, in relation to the needle guard 120.

As again shown in FIG. 10B (which shows the needle 16 and the needle guard 120 removed from the catheter hub 26 and is thus applicable to both the embodiment of FIG. 10A and the embodiment of FIG. 14), the needle guard 120 is fixedly attached to the needle 16 after needle retraction, such that the needle guard and the needle can be removed from the catheter hub as a unitary assembly and safely discarded. If an attempt is made, either intentionally or inadvertently, to pull the needle further to the right (as viewed in FIG. 10B) out of the needle guard, the crimp 138 on the needle shaft will come into contact with the end wall 126, and, since the crimp width is greater than the diameter of the opening 134, the end wall 126 will, at this point, prevent any further axial movement of the needle out of the needle guard.

As shown in FIG. 16, the inwardly extending, generally annular protrusion 136b may alternatively be formed to have a generally C-shaped configuration. Optionally, the C-shaped protrusion 136b may be defined by a metal snap ring which is partially disposed within a groove, such as groove 136 of FIG. 10a. Thus, the inwardly extending, generally annular protrusion 136b may be formed by sliding a metal snap ring into the catheter hub 26 until the metal snap ring snaps into a groove formed within the catheter hub 26.

As shown in FIG. 17, as a further alternative the inwardly extending, generally annular protrusion 136c may be defined so as to have two generally semi-circular segments or portions.

Indeed, those skilled in the art will appreciate that various different configurations of the inwardly extending, generally annular protrusion are likewise suitable.

Thus, the inwardly extending, generally annular protrusion may have any desired configuration. It is preferred that the inwardly extending, generally annular protrusion not have any gap(s) 137 (as shown in FIGS. 16 and 17) which have a width greater than the width of the distal end walls 130 of the needle guard 120. Sizing the gaps 137 so as to be smaller than the width of the end walls tends to prevent the needle guard 120 from passing through such gaps 137 and thereby undesirably allowing the needle guard 120 to slip out of the needle hub 26 without properly protecting the tip 18 of the needle 16. Thus, according to the present invention, any desired number of separate sections may be utilized to define the inwardly extending, generally annular protrusion, as long as the needle guard 120 is effectively held in place thereby as the needle 14 is withdrawn from the catheter 24.

As shown in FIGS. 18 and 19, the crimp 138 formed in the needle 16 preferably defines a pair of generally opposed, outwardly extending bulges 138a in the needle and also defines a pair of generally opposed, inwardly extending depressions 138b, which are disposed generally orthogonally with respect to the bulges 138a. The bulges 138a define a crimp 138 having a width, dimension W, which is small enough to facilitate movement of the needle 16 within the catheter 24, as shown in FIG. 14, and which is too large to pass through the central opening 134 formed in the end wall 126 of the needle guard 120, as discussed above.

The crimp 138 may be formed by any contemporary crimping process, such as those processes wherein two jaws of a vise or crimper come together so as to squeeze the needle 16 in a manner which forms the depressions 138b of FIG. 19, thereby consequently also forming the bulges 138a.

The IV catheter shown in FIG. 14 is assembled by sliding the needle guard 120 over the sharpened tip 18 of the needle 16 before the crimp 138 is formed in the needle 16. The needle 16 passes through the opening 134 formed in the end wall 126 of the needle guard 120. The distal arms 132 are opened and the needle 16 passes through them. Next, the crimp 138 is formed in the needle 16, so that the needle guard 120 is captured between the crimp 138 and the needle hub 12.

Next, the needle 16, having the needle guard 120 thereon, is slid into the catheter hub 26 such that the sharpened tip 18 of the needle 16 enters the catheter 24. The needle 16 is slid into the catheter 24 until the curved protrusions 128 of the needle guard 120 abut the annular protrusion 136A.

Once the curved protrusions 128 abut the annular protrusion 136A, the needle guard 120 ceases to move along with the needle 16. The needle guard 120 may cease to move along with the needle 16 before the curved protrusions 128 of the needle guard 120 abut the annular protrusion 136A, since the inner surface of the catheter hub 26 tapers inwardly, such that the inside diameter thereof is reduced as the needle guard 120 travels further into the catheter hub 26. Thus, the needle guard 120 may cease moving along with the needle 16 due to such narrowing of the inside of the needle guard 26, when the inside diameter of the catheter hub 26 becomes too small for the needle guard 120 to pass further therethrough.

Once the needle guard 120 has ceased to move along with the needle 16 as the needle is inserted into the catheter 24, a tool is used to gently urge the needle guard 120 further into the catheter hub 26, until the curved protrusions 128 of the needle guard 120 pass beyond the annular protrusion 136A. Sufficient force must be applied to the needle guard 120 via the tool so as to cause the curved protrusions of the needle guard 120 to flex toward one another such that they pass beyond the annular protrusion 136A.

After the curved protrusions 128 of the needle guard 120 have passed beyond the annular protrusion 136A and have flexed back outwardly, generally so as to contact the inner wall of the catheter hub 26, then the needle guard 120 is in the ready position as shown in FIG. 14.

Figure 20:
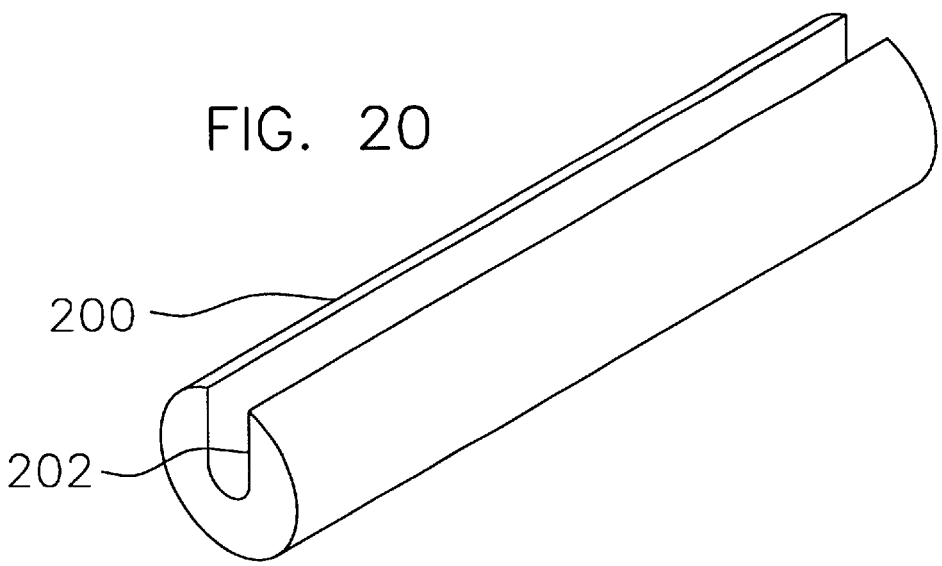
FIG. 20 is a semi-schematic perspective view of a tool used for assembling one configuration of the present invention.

The tool used to urge the needle guard 120 past the annular protrusion 136 within the catheter hub 26 may comprise any convenient structure suitable for such use. For example, as shown in FIG. 20, a simple pin 200 with a slot 202 running the length thereof (so as to receive the needle 16 as the needle guard 120 is pushed) may suffice.

Thus, when the IV catheter of the present invention is assembled, the curved protrusions 128 of the needle guard 120 positively engage the inwardly extending annular protrusion 136A such that the needle guard 120 remains within the catheter hub 26 as the needle 16 is withdrawn from the catheter 24, until the sharpened tip 18 of the needle passes between the lips 132 of the needle guard 120 so as to disengage the curved protrusions 128 with respect to the annular protrusion 136A to allow the needle guard 120 to move out of the catheter hub 26 along with the needle 16.

An alternative method for assembling the spring clip safety I.V. catheter of the present invention may be utilized when the annular protrusion is configured as a C-shaped protrusion or an open ring 136b, as shown in FIG. 16 and is formed separately from the catheter hub 26. In this instance, the open ring 136b can be placed upon the needle guard 120 (between the proximal and distal ends thereof) after the needle 16 has been passed through the needle guard 120 and crimped. Then, both the needle guard 120 and the open ring 136b may be simultaneously pushed into the catheter hub 26 utilizing the same tool.

This tool preferably has at least two fingers, one of which which extends along each side of the needle guard 120, so as to push the open ring 136b further into the catheter hub 26 than the proximal end of the needle guard 120. In this manner, the needle guard 120 does not have to be pushed over the annular protrusion 136. Rather, the needle guard 120 and the annular protrusion 136b are assembled together, i.e., along with one another. The annular protrusion 136b is thus assembled into the catheter hub 26 so as to lock the needle guard 120 into position, where the needle guard 120 remains until the needle 16 is moved to the protective position thereof, as discussed in detail above.

Figure 21:
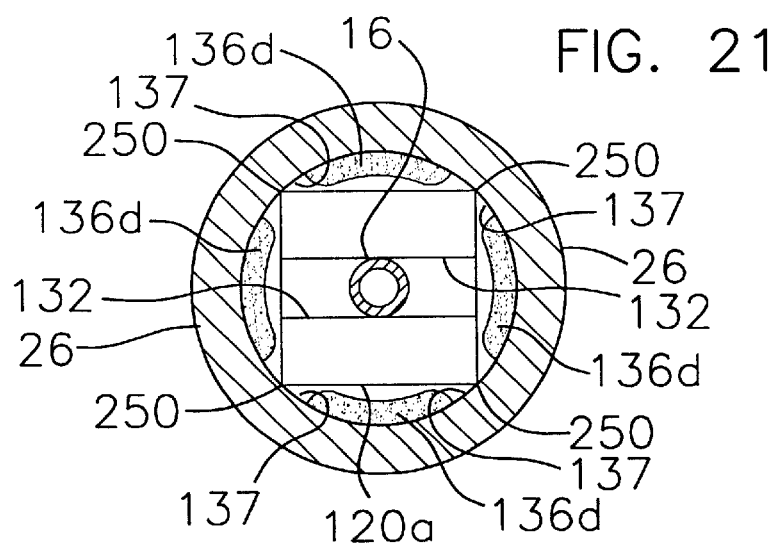
FIG. 21 is a semi-schematic end view of alternative configuration of the present invention showing the needle guard oriented so as to facilitate insertion within the catheter hub.
Figure 22:
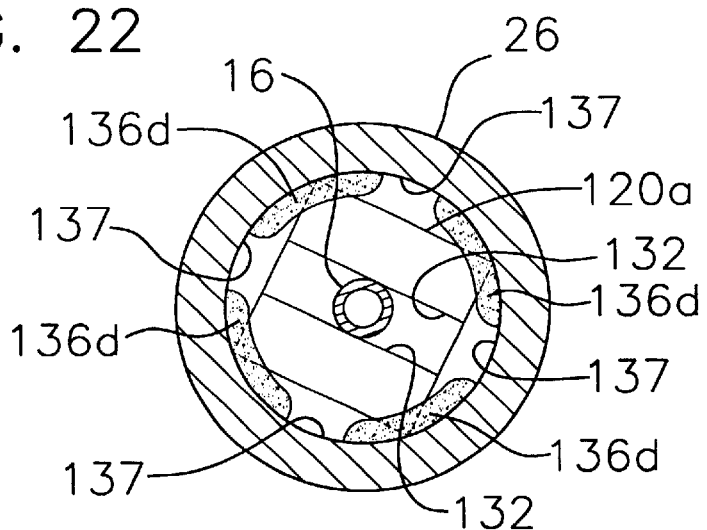
FIG. 22 is a semi-schematic end view of the alternative configuration of FIG. 21, showing the needle guard after it has been rotated so as to remain within the catheter hub until the needle is moved to the protected position thereof.

Referring now to FIGS. 21 and 22, yet a further alternative method for assembling the needle guard 120a into the catheter hub 26 is shown. According to this alternative method, the annular protrusion 136d is configured so as to have at least four openings 137 formed therein and is configured so that the needle guard 120a may pass through the openings 137 utilizing very little or no insertion force. After the needle guard 120a has been pushed into the catheter hub 26 past the annular protrusion 136d, then the needle guard 120a is rotated so as to position the four corners 250 thereof behind the annular protrusion 136d as shown in FIG. 22, which then functions so as to maintain the needle guard 120a with the catheter hub 26 until the needle 16 is withdrawn and moved into the protective position thereof, as discussed in detail above.

It may be desirable to form the needle guard 120a so as to provide a generally square profile, as shown in FIGS. 21 and 22. However, as those skilled in the art will appreciate, various different generally square, rectangular or other profiles of the needle guard 120a are likewise suitable. It is merely necessary to locate the openings 137 formed in the annular protrusion 136d such that the needle guard 120a is readily received therebetween during the assemble process and is then held in place thereby, after rotating the needle guard 120a so as to place the corners 250 thereof into abutting contact with the annular protrusion 136d.

It will thus be appreciated that the spring clip needle guard of the invention as employed in an IV catheter provides automatic and reliable protection of the needle tip upon needle retraction to prevent accidental contact with the needle tip by a healthcare practitioner. It will also be appreciated that modifications may be made to the embodiments of the invention specifically described hereinabove without necessarily departing from the spirit and scope of the invention.

What is claimed is:

1. An IV catheter apparatus comprising a tubular catheter having a proximal end and a distal end, a needle having a needle shaft and a tip, said needle being received within said tubular catheter when in a ready position, a catheter hub attached to the proximal end of said catheter, said catheter hub having a hollow interior and an inner wall, said needle being movable between said ready position in which said tip is outside of said catheter hub and a retracted position in which said tip is within the interior of said catheter hub, a unitary needle guard positioned in the interior of said catheter hub and including a resilient portion engaged by said needle shaft when said needle is in its said ready position, a section of said resilient portion of said needle guard being urged by said needle shaft into contact with an interior wall of said catheter hub when said needle is in its said ready position, and an inwardly extending, generally annular protrusion formed on said interior wall of said catheter hub for engaging a segment of said needle guard for retaining said needle guard to said catheter hub during the movement of said needle between its said ready position and its said retracted position, said needle guard including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that contact between said section of said needle guard and said catheter hub is released.

2. The IV catheter apparatus of claim 1, in which said distal wall of said needle guard is contiguous with said resilient portion, said distal wall terminating at a curved lip engaging the underside of said needle shaft when said needle is in its said ready position.

3. The IV catheter apparatus of claim 2, wherein the needle guard further includes an upper end contiguous with the transverse segment and proximal to the resilient portion and in contact with an opposed interior wall of the catheter hub when the needle is in the ready position.

4. The IV catheter apparatus of claim 1, in which said needle guard further includes an upper end proximal to said resilient portion and in contact with an opposed interior wall of the catheter hub in said ready position.

5. The IV catheter apparatus of claim 2, in which said needle guard further includes an upper end proximal to said resilient portion and in contact with an opposed interior wall of the catheter hub when said needle is in its said ready position.

6. The IV catheter apparatus of claim 1, in which said needle guard further comprises a proximal arm having a lower curved segment in contact with an inner wall of said catheter hub when said needle is in its said ready position.

7. The IV catheter apparatus of claim 6, in which said proximal arm further includes an upper end in engagement with an opposed location of said inner wall of said catheter hub distal to the point of contact with said lower curved segment when said needle is in its said ready position.

8. The IV catheter apparatus of claim 7, in which said needle guard further comprises a proximal end wall having an opening for receiving said needle therethrough, said needle further comprising an increased width segment on the needle shaft inward of said needle tip, the width of said increased width segment being greater than that of said opening in said proximal end wall.

9. The IV catheter apparatus of claim 8, in which said needle includes a circumferential groove forced inwardly of said tip, said finger being adapted to enter into said groove in the event an axial force is applied to said needle in the proximal direction when said needle guard is in its said blocking position.

10. The IV catheter apparatus of claim 1, in which said needle guard includes first and second distal walls which overlap one another and form a distal barrier to said needle when said needle guard is in its said blocking position.

11. The IV catheter apparatus of claim 10, in which said needle guard further comprises a proximal end wall having an opening for receiving said needle therethrough and first and second arms extending respectively between said proximal end wall and said first and second distal walls.

12. The IV catheter apparatus of claim 11, in which each of said arms includes a wide section hingedly secured to said first and second distal walls and a narrow section extending from said wide section to said end wall.

13. The IV catheter apparatus of claim 12, in which said needle includes a increased width segment on the needle shaft inward of said needle tip, the width of said increased width segment being greater than that of said opening in said proximal end wall.

14. The IV catheter apparatus of claim 12, in which said needle guard includes a proximal end wall extending from said resilient portion and including an opening allowing said needle to pass therethrough, said needle further including an increased width segment on the needle shaft inward of said needle tip, the width of said increased width segment being greater than that of said opening in said proximal end wall.

15. The IV catheter apparatus of claim 14, in which said needle guard further comprises a proximal end wall having an opening for receiving said needle therethrough, said needle further comprising an increased width segment on the needle shaft inward of said needle tip, the width of said increased width segment being greater than that of said opening in said proximal end wall.

16. An IV catheter apparatus comprising a tubular catheter having a proximal end and a distal end, a needle having a needle shaft and a tip, said needle being received within said tubular catheter when in a ready position, a catheter hub attached to the proximal end of said catheter, said catheter hub having a hollow interior and an inner wall, said needle being movable between said ready position in which said tip is outside of said catheter hub and a retracted position in which said tip is within the interior of said catheter hub, a unitary needle guard positioned in the interior of said catheter hub and including a resilient portion engaged by said needle shaft when said needle is in its said ready position, a section of said resilient portion of said needle guard being urged by said needle shaft into contact with an interior wall of said catheter hub when said needle is in its said ready position, an inwardly extending, generally annular protrusion formed on said interior wall of said catheter hub for engaging a segment of said needle guard for retaining said needle guard to said catheter hub during the movement of said needle between its said ready position and its said retracted position, said needle guard including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that retaining contact between said section of said needle guard and said catheter hub is released.

17. The IV catheter apparatus of claim 16 inwhich said distal wall of said needle guard is contiguous with said resilient portion, said resilient portion including a curved lip engaging side of said needle shaft when said needle is in its said ready position.

18. The IV catheter apparatus of claim 16, which said resilient portion comprises a transverse arm and a curved upper segment contiguous with said transverse arm and in contact with an opposed interior wall of the catheter hub when said needle is in its said ready position.

19. The IV catheter apparatus of claim 16, in which said needle guard further comprises a proximal wall having a lower curved segment in contact with said interior wall of said catheter hub when said needle is in its said ready position.

20. The IV catheter apparatus of claim 19, in which said proximal wall further includes an upper end in engagement with an opposed location of said interior wall of said catheter hub when said needle guard is in its said ready position.

21. The IV catheter apparatus of claim 16, in which said needle guard includes first and second distal walls which overlap one another and form a distal barrier to said needle when said needle guard is in its said blocking position.

22. The IV catheter apparatus of claim 21, in which each of said distal walls includes a curved lip engaging opposing surfaces of said needle shaft when said needle is in its said ready position.

23. The IV catheter apparatus of claim 22, in which said first and second distal walls each further include a wide section and a narrow section extending from said wide section toward said proximalend wall.

24. The IV catheter apparatus of claim 21, in which said needle guard further comprises a proximal end wall having an opening for receiving said needle therethrough and first and second arms extending respectively between said proximal end wall and said first and second distal walls.

25. The IV catheter apparatus of claim 24, in which said needle includes an increased width segment on the needle shaft inward of said needle tip, the width of said increased width segment being greater than that of said opening in said proximal end wall.

26. The IV catheter apparatus of claim 25, in which said first and second distal walls each further include a wide section and a narrow section extending from said wide section toward said proximal end wall.

27. An IV catheter apparatus comprising a tubular catheter having a proximal end and a distal end, a needle having a needle shaft and a tip, said needle being received within said tubular catheter when in a ready position, catheter hub attached to the proximal end of said catheter, said catheter hub having a hollow interior and an inner wall, said needle being movable between said ready position in which said tip is outside of said catheter hub and a retracted position in which said tip is within the interior of said catheter hub, and a unitary needle guard substantially positioned in the interior of said catheter hub and including a resilient portion engaged by said needle shaft when said needle is in said ready position, a section of said resilient portion of said needle guard being urged by said needle shaft into retaining contact with an inwardly extending, generally annular protrusion formed upon an interior wall of said catheter hub when said needle is in its said ready position, said needle guard also including a distal wall extending from said resilient portion and spaced from said needle tip when said needle is in its said ready position and movable within the interior of said catheter hub to a blocking position distal of said needle tip when said needle is in its said retracted position in which said needle shaft no longer exerts a force on said resilient portion of said needle guard such that said retaining contact between said section of said needle guard and said catheter hub is released upon the movement of said needle guard to its said blocking position.

28. The IV catheter apparatus of claim 27, in which said needle guard includes first and second distal walls which overlap one another and form a distal barrier to said needle when said needle guard is in its blocking position.

29. The IV catheter apparatus of claim 28, in which said first and second distal walls include a wide section and a narrow section extending from said wide section toward said proximal end wall.

30. The IV catheter apparatus of claim 29, in which said needle guard further comprises a proximal end wall having an opening for receiving said needle therethrough and first and second arms extending respectively between said proximal end wall and said first and second distal walls.

31. The IV catheter apparatus of claim 30, in which said needle includes an increased width segment on the needle shaft inward of said needle tip, the width of said increased width segment being greater than that of said opening in said proximal end wall.

32. A catheter device comprising at least two components that are separable from one another, the first component comprises a catheter hub and a catheter tube fixedly secured thereto; and the second component comprises a needle hub and a needle fixedly secured thereto; wherein the needle comprises a needle tip, a large diameter segment, and a needle shaft, and the catheter tube comprises a catheter passage; and wherein the catheter hub and the needle hub further comprise:

a catheter hub distal end and a catheter hub proximal end, the catheter hub distal end having the catheter tube extending therefrom;

a catheter hub opening, the catheter hub opening defining a catheter hub annular space;

a needle hub distal end and a needle hub proximal end, the needle hub distal end having the needle extending therefrom;

a needle protector clip having a resilient biasing portion; wherein when the needle is in the ready position, which is the position in which the needle projects into the catheter passage and the needle tip extends beyond the catheter tube; the needle protector clip is disposed over the needle and is located within the catheter hub annular space but spaced apart from the needle hub distal end; and wherein when the needle is in a fully retracted position, which is the position in which the needle protector clip moves relative to the needle until the needle is completely withdrawn from the catheter hub annular space, the needle protector clip is activated and attaches to the needle at the needle tip and the large diameter segment; and wherein the resilient biasing portion has a first position and a second position, the first position is characterized by the resilient biasing portion abutting the needle shaft and the second position is characterized by the resilient biasing portion shielding the needle tip and preventing accidental contact with the needle tip.

33. The catheter device of claim 32, wherein the needle protector clip further comprises a protector clip proximal end and a protector clip distal end, and wherein the protector clip is secured to the needle tip when the needle is in the fully retracted position by a portion of the protector clip proximal end making contact with the large diameter segment and a portion of the protector clip distal end shielding the needle tip.

34. The catheter device of claim 32, further comprising a needle protector clip outer contact surface, and wherein the needle protector clip is secured to the catheter hub annular space by frictionally engaging the needle protector clip outer contact surface with a surface located within the catheter hub annular space; the needle protector clip is configured to separate from the catheter hub annular space when the frictional engagement is removed.

35. The catheter device of claim 32, wherein the large diameter segment is a crimp.

36. A catheter device comprising:
   a needle hub having a needle hub proximal end and a needle hub distal end; the needle hub distal end is secured to a needle at the needle's proximal end, the needle has a needle tip, a needle shaft, and a needle crimp disposed proximal of the needle tip;
   a catheter hub having a catheter hub proximal end and a catheter hub distal end; the catheter hub distal end is secured to a catheter tube at the catheter tube's proximal end;
   the catheter tube has an opening at a catheter tube distal end and the catheter tube proximal end, and a catheter tube annular space defined between the two openings;
   wherein the needle and the crimp are disposed within the catheter tube annular space and the needle tip extends beyond the annular space when the needle is in a ready position; and
   a needle protector for shielding the needle tip and preventing accidental contact with the needle tip when the needle is in a fully retracted position, the needle protector is located adjacent to but spaced apart from the needle hub distal end, the needle protector comprising an opening for allowing the needle to slide from between the ready position and the fully retracted position, the needle protector further comprising a protector arm and a protector arm first position and second position, the protector arm first position is a position in which the protector arm is in a flexed state and contacts the needle shaft and the protector arm second position is a position in which the protector arm is in a relaxed state and the needle protector is shielding the needle tip and preventing accidental contact with the needle tip.

37. The catheter device of claim 36, wherein the needle protector clip further comprises a protector clip proximal end and a protector clip distal end, wherein the protector clip is secured to the needle tip when the needle is in the fully retracted position by a portion of the protector clip proximal end making contact with the needle crimp and a portion of the protector clip distal end shielding the needle tip.

38. The catheter device of claim 36, further comprising a needle protector clip outer contact surface, and wherein the needle protector clip is secured to the catheter hub annular space by frictionally engaging the needle protector clip outer contact surface with a surface located within the catheter hub annular space; the needle protector clip is configured to separate from the catheter hub annular space when the frictional engagement is removed.

39. An IV catheter apparatus comprising a tubular catheter having a proximal end and a distal end, a needle having a needle shaft and a tip and wherein the needle is attached to a distal end of a needle hub, said needle being received within said tubular catheter when the needle is in a ready position, a catheter hub attached to the proximal end of said catheter, said catheter hub having a hollow interior and an inner wall, said needle being movable between said ready position in which said tip is outside of said catheter hub and a retracted position in which said tip is within the interior of said catheter hub, a needle guard positioned in the interior of said catheter hub in a spaced apart relationship from the distal end of the needle hub; and wherein the needle guard comprises a resilient portion engaged by said needle shaft when said needle is in its ready position, the needle guard resilient portion is movable within the interior of said catheter hub to a blocking position distal of said needle tip when said needle is in its retracted position in which said needle shaft no longer exerts a force on said resilient portion of said needle guard.

40. The IV catheter apparatus of claim 39, wherein the needle guard further comprises a needle guard proximal end, wherein the needle guard is secured to the needle tip when the needle is in the fully retracted position by a portion of the needle guard proximal end making contact with a needle crimp and the resilient portion blocking the needle tip.

41. The IV catheter apparatus of claim 39, further comprising a needle guard outer contact surface, and wherein the needle guard is secured to the catheter hub hollow cylinder by frictionally engaging the needle guard outer contact surface with the inner wall of the hollow cylinder; the needle guard is configured to separate from the hollow cylinder when the frictional engagement is removed.

42. A combination needle and needle guard having a ready position and a retracted position comprising:
   a needle hub mechanically coupled to the needle having a needle tip, the needle hub comprising an open proximal end, an interior cavity, and a closed distal end, wherein the needle is attached to the distal end and is in communication with the interior cavity and projects distally away from the needle hub;
   a unitary needle guard positioned on and coaxial with the needle, the unitary needle guard comprising an end wall having an end wall opening and having the needle passing therethrough, a resilient portion extending from the end wall and having a distal wall at the end thereof, the distal wall and the resilient portion defining an intersection therebetween that comprises a curved protrusion, wherein a portion of the distal wall is adapted to contact a side of the needle and urges the resilient portion radially outwardly from the needle when the combination needle and needle guard is in the ready position;
   an outer hub comprising a housing comprising a proximal end having a proximal end opening, a distal end having a distal end opening, a hub exterior surface and a hub interior cavity; the hub interior cavity comprising an interior surface that includes a projection, wherein the interior cavity defines a first larger diameter and the projection defines a second smaller diameter;
   the combination needle and needle guard is configured such that when the combination is in the ready position, the needle guard is positioned within the hub interior cavity and the needle and needle guard are coaxially disposed, the curved protrusion at the intersection between the distal wall and the resilient portion is positioned distal of the interior surface projection, the needle guard is positioned adjacent the closed distal end of the needle hub, and the outer hub proximal end is adjacent the closed distal end of the needle hub; and the combination needle and needle guard is configured such that in transitioning between the ready position and the retracted position, the outer hub moves distally relative to the needle, whereby the interior surface projection contacts the curved protrusion of the needle guard thereby moving the needle guard distally until the needle guard distal wall moves past the needle tip, whereupon the resilient portion snaps radially inwardly to guard the needle tip, the curved protrusion disengages from the interior surface projection, and the outer hub separates from the needle guard and the needle.

43. The combination needle and needle guard of claim 42, wherein a the outer hub proximal end is engaged to the closed distal end of the needle hub.

44. The combination needle and needle guard of claim 42, further comprising a needle crimp located proximally of the needle tip, wherein the end wall opening of the unitary needle guard contacts the needle crimp when the combination needle and needle guard is in the retracted position.

45. The combination needle and needle guard of claim 42, wherein the distal wall of the unitary needle guard further comprises a curved lip portion, and wherein the curved lip portion contacts the side of the needle to urge the resilient portion radially outwardly from the needle.

46. The combination needle and needle guard of claim 42, further comprising a catheter tube attached to the distal end opening of the outer hub.

47. The combination needle and needle guard of claim 42, wherein the end wall of the unitary needle guard is in a spaced apart configuration from the closed distal end of the needle hub.

48. An IV catheter assembly having a ready position and a retracted position comprising:

a needle hub mechanically coupled to the needle having a needle tip, the needle hub comprising an open proximal end, an interior cavity, and a closed distal end, wherein the needle is attached to the closed distal end and is in communication with the interior cavity and projects distally away from the needle hub;

a unitary needle guard positioned on and coaxial with the needle, the unitary needle guard comprising an end wall having an end wall opening and having the needle passing therethrough, a resilient portion extending from the end wall and having a distal wall at the end thereof, the distal wall and the resilient portion defining an intersection therebetween that comprises a curved protrusion, wherein a portion of the distal wall contacts a side of the needle and urges a portion of the resilient portion radially outwardly from the needle when the combination needle and needle guard is in the ready position;

an outer hub comprising a housing comprising a proximal end having a proximal end opening, a distal end having a distal end opening, a hub exterior surface and a hub interior cavity; the hub interior cavity comprising an interior surface that includes a projection, wherein the interior cavity defines a first larger diameter and the projection defines a second smaller diameter;

wherein when the combination needle and needle guard is in the ready position, the needle guard is positioned within the hub interior cavity and the needle and needle guard are coaxially disposed, the curved protrusion at the intersection between the distal wall and the resilient portion is positioned distal of the interior surface projection, the needle guard is positioned adjacent the closed distal end of the needle hub, and the outer hub proximal end is adjacent the closed distal end of the needle hub; and wherein when the combination needle and needle guard transitions between the ready position and the retracted position, the outer hub moves distally relative to the needle, whereby the interior surface projection contacts the curved protrusion of the needle guard thereby moving the needle guard distally until the needle guard distal wall moves past the needle tip, whereupon the resilient portion snaps radially inwardly to guard the needle tip, the curved protrusion disengages from the interior surface projection, and the outer hub separates from the needle guard and the needle.

49. The IV catheter assembly of claim 48, wherein the outer hub proximal end is engaged to the closed distal end of the needle hub.

50. The IV catheter assembly of claim 48, further comprising a needle crimp located proximally of the needle tip, wherein the end wall opening of the unitary needle guard contacts the needle crimp when the combination needle and needle guard is in the retracted position.

51. The IV catheter assembly of claim 48, wherein the distal wall of the unitary needle guard further comprises a curved lip portion, and wherein the curved lip portion contacts the side of the needle to urge the resilient portion radially outwardly from the needle.

52. The IV catheter assembly of claim 48, further comprising a catheter tube attached to the distal end opening of the outer hub.

53. The IV catheter assembly of claim 48, wherein the end wall of the unitary needle guard in a spaced apart configuration from the closed distal end of the needle hub.

* * * * *

(12) EX PARTE REEXAMINATION CERTIFICATE (7172nd)
United States Patent
Woehr et al.

(10) Number: US 6,616,630 C1
(45) Certificate Issued: Nov. 17, 2009

(54) SPRING CLIP SAFETY IV CATHETER

(75) Inventors: Kevin Woehr, Felsberg (DE); Manfred Orth, Kassel (DE); Mark Wynkoop, Coopersberg, PA (US)

(73) Assignee: B. Braun Melsungen AG, Melsungen (DE)

Reexamination Request:
No. 90/010,474, Mar. 27, 2009

Reexamination Certificate for:
Patent No.: 6,616,630
Issued: Sep. 9, 2003
Appl. No.: 09/638,641
Filed: Aug. 14, 2000

Related U.S. Application Data

(63) Continuation of application No. 09/183,697, filed on Oct. 30, 1998, now Pat. No. 6,287,278, which is a continuation-in-part of application No. 09/097,170, filed on Jun. 12, 1998, now Pat. No. 6,117,108, which is a continuation-in-part of application No. 08/915,148, filed on Aug. 20, 1997, now abandoned.

(51) Int. Cl.
*A61M 5/00* (2006.01)

(52) U.S. Cl. ...................................... 604/110; 604/263
(58) Field of Classification Search ....................... None
See application file for complete search history.

(56) References Cited

U.S. PATENT DOCUMENTS 5,135,504 A * 8/1992 McLees ...................... 604/164

* cited by examiner

*Primary Examiner*—Beverly M. Flanagan

(57) ABSTRACT

A safety IV catheter includes a unitary, resilient needle guard received in a catheter hub. The needle guard includes a proximal arm or wall that includes an opening through which a needle passes for axial movement. When the needle is retracted from the catheter, it releases the force that had previously prevented movement of the needle guard within the catheter hub. This in turn causes the needle guard to snap into a position in which it is clamped onto the needle shaft and in which its distal wall blocks access to the needle tip. In this condition, the spring needle guard and needle can be removed from the catheter hub. A slot or crimp may be formed in the needle shaft that engages with the needle guard after the protected needle and needle guard are removed from the catheter hub.

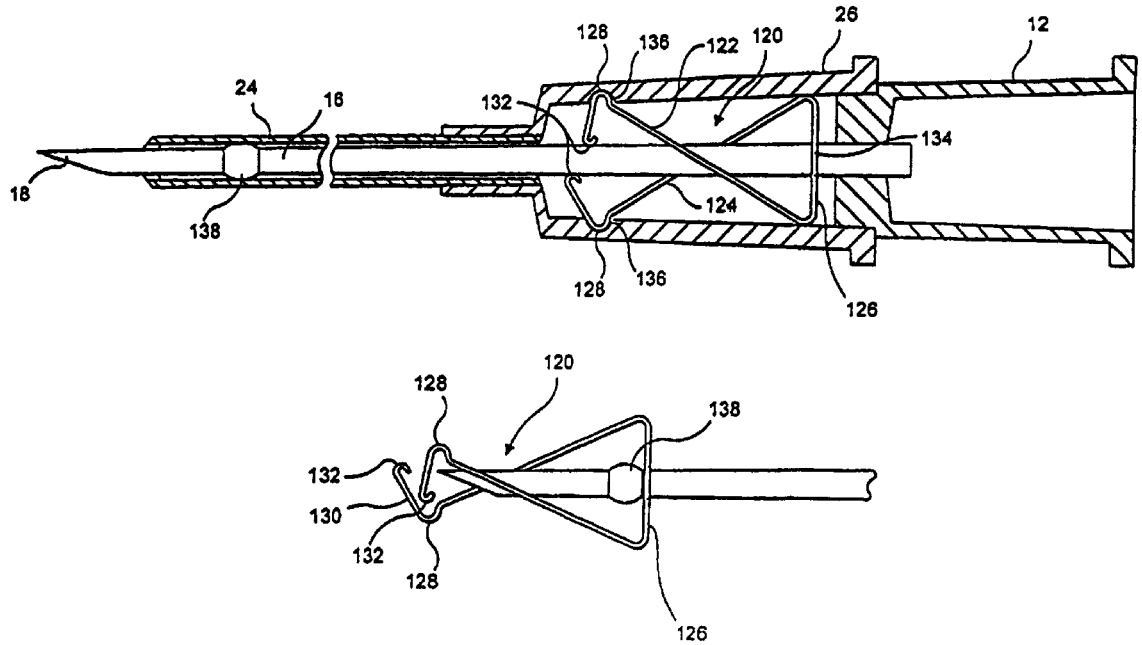

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 41 is cancelled.

Claim 39 is determined to be patentable as amended.

Claims 1–38, 40 and 42–53 were not reexamined.

39. An IV catheter apparatus comprising a tubular catheter having a proximal end and a distal end, a needle having a needle shaft and a tip and wherein the needle is attached to a distal end of a needle hub, said needle being received within said tubular catheter when the needle is in a ready position, a catheter hub attached to the proximal end of said catheter, said catheter hub having a hollow interior and an inner wall, said needle being moveable between said ready position in which said tip is outside of said catheter hub and a retracted position in which said tip is within the interior of said catheter hub, a needle guard positioned in the interior of said catheter hub in a spaced apart relationship from the distal end of the needle hub; [and]

wherein the needle guard comprises a resilient portion engaged by *a side of* said needle shaft when said needle is in its ready position, the needle guard resilient portion is movable within the interior of said catheter hub to a blocking position distal of said needle tip when said needle is in its retracted postion in which said needle shaft no longer exerts a force on said resilient portion of said needle guard*; and*

*wherein an outer contact surface on the needle guard is secured to a groove formed in the catheter hub hollow interior when the resilient portion is engaged by the side of the needle shaft and biased radially outwardly.*

\* \* \* \* \*